(12) United States Patent
Trevethick

(10) Patent No.: US 9,340,802 B2
(45) Date of Patent: May 17, 2016

(54) FERMENTATION OF GASEOUS SUBSTRATES

(71) Applicant: LanzaTech New Zealand Limited, Auckland (NZ)

(72) Inventor: Simon Richard Trevethick, Whitianga (NZ)

(73) Assignee: LANZATECH NEW ZEALAND LIMITED, Auckland (NZ)

(*) Notice: Subject to any disclaimer, the term of this patent is extended or adjusted under 35 U.S.C. 154(b) by 14 days.

(21) Appl. No.: 14/309,864

(22) Filed: Jun. 19, 2014

(65) Prior Publication Data

US 2014/0377826 A1    Dec. 25, 2014

Related U.S. Application Data

(60) Provisional application No. 61/837,626, filed on Jun. 20, 2013.

(51) Int. Cl.
*C12P 7/06* (2006.01)
*C12M 1/00* (2006.01)

(52) U.S. Cl.
CPC .............. *C12P 7/065* (2013.01); *C12M 29/18* (2013.01)

(58) Field of Classification Search
None
See application file for complete search history.

(56) References Cited

U.S. PATENT DOCUMENTS

| 5,173,429 | A | 12/1992 | Gaddy et al. |
| 5,593,886 | A | 1/1997 | Gaddy |
| 5,807,722 | A | 9/1998 | Gaddy |
| 5,821,111 | A | 10/1998 | Grady et al. |
| 5,938,333 | A | 8/1999 | Kearney |
| 6,136,577 | A | 10/2000 | Gaddy |
| 6,333,019 | B1 | 12/2001 | Coppens |
| 6,340,581 | B1 | 1/2002 | Gaddy |
| 6,368,819 | B1 | 4/2002 | Gaddy et al. |
| 6,742,924 | B2 | 6/2004 | Kearney |
| 6,753,170 | B2 | 6/2004 | Gaddy et al. |
| 7,078,201 | B2 | 7/2006 | Burmaster |

(Continued)

FOREIGN PATENT DOCUMENTS

| EP | 117309 EP | 5/1984 |
| WO | WO98/00558 | 1/1998 |

(Continued)

OTHER PUBLICATIONS

Kreutzer "Shouldn't catalysts shape up? Structured reactors in general and gas-liquid monolith reactors in particular" Catalysis Today, (2006) vol. 111, 111-118.*

(Continued)

*Primary Examiner* — Robert Yamasaki
*Assistant Examiner* — Charles Zoltan Constantine
(74) *Attorney, Agent, or Firm* — Frank S Molinaro

(57) ABSTRACT

Processes, as well as associated systems, are disclosed for the biological conversion of CO into desired end products such as ethanol. The use of a plurality of perforated plates, for example in the riser section of a bioreactor, which are positioned substantially horizontally and normal to the upward flow of both a CO-containing substrate and liquid culture medium, can significantly improve CO utilization of the bacteria and consequently the overall process economics. The geometry of apertures in the perforated plates is an important determinant of their performance, with fractal patterns and other multi-edged shapes leading to particularly advantageous results.

16 Claims, 14 Drawing Sheets

(56) References Cited

U.S. PATENT DOCUMENTS

| | | | |
|---|---|---|---|
| 8,178,330 B2 * | 5/2012 | Trevethick | ............. C12M 21/12 435/161 |
| 8,309,348 B2 | 11/2012 | Tsai et al. | |
| 2011/0244538 A1 | 10/2011 | Trevethick | |
| 2013/0284830 A1 * | 10/2013 | Wells | ........................ B05B 1/14 239/601 |

FOREIGN PATENT DOCUMENTS

| | | |
|---|---|---|
| WO | WO00/68407 | 11/2000 |
| WO | WO02/08438 | 1/2002 |
| WO | WO02/092207 | 11/2002 |
| WO | WO2007/113335 | 10/2007 |
| WO | WO2007/117157 | 10/2007 |
| WO | 2008040365 A1 | 4/2008 |
| WO | WO2008/115080 | 9/2008 |
| WO | WO2009/124939 | 10/2009 |
| WO | 2012042245 A1 | 4/2012 |
| WO | WO2012/042245 | 4/2012 |

OTHER PUBLICATIONS

PCT (PCT/NZ2014/000122) Search Report dated Nov. 13, 2014.
Abrini, J. et al., Archives of Microbiology, (1994), 161, 345-351.
Hensirisak et al., Scale-up of microbubble dispersion generator for aerobic fermentation, Applied Biochemistry and Biotechnology, Oct. 2002, vol. 101, No. 3.
Klasson K. T. et al., Bioconversion of synthesis gas into liquid or gaseous fuels, Enzyme and Microbial Technology, (1992), 14, 602-608.
Klasson K. T. et al., Bioreactors for synthesis gas fermentations resources, Conservation and Recycling, (1991), 5, 145-165.
Klasson, K. T. et al., Bioreactor design for synthesis gas fermentations, Fuel, (1991), 70, 605-614.
Liou et al., International Journal of Systematic and Evolutionary Microbiology, (2005), 33, pp. 2085-2091.
Sakai et al., Biotechnology Letters, (2004), 29, pp. 1607-1612.
Svetlichny, V.A. Sokolova T.G. et al., Systematic and Applied Microbiology, (1991), 14, 254-260.
Vega, J. L. et al., Design of Bioreactors for Coal Synthesis Gas Fermentations, Resources, Conservation and Recycling, (1990), 3. 149-160.
Vega, J. L. et al., Study of Gaseous Substrate Fermentation: Carbon Monoxide Conversion to Acetate. 2. Continuous Culture. Biotech. Bioeng., (1989), 34. 6. 785-793.
Vega, J. L., et al., Study of gaseous substrate fermentations: Carbon monoxide conversion to acetate. 1. Batch culure, Biotechnology and Bioengineering, (1989), 34. 6. 774-784.

* cited by examiner

FERMENTATION OF GASEOUS SUBSTRATES

CROSS-REFERENCE TO RELATED APPLICATIONS

This application is a non-provisional application under 35 U.S.C. §111(a) and claims the benefit of priority under 35 U.S.C. §119(e) to U.S. provisional application No. 61/837,626, filed Jun. 20, 2013, which is hereby incorporated by reference in its entirety.

FIELD OF THE INVENTION

The invention relates to systems, apparatuses and methods for improving gas utilization or consumption by a bacterial culture during a two-phase (gas-liquid) fermentation process. A representative embodiment utilizes a perforated plate or series of perforated plates, wherein the apertures of said plate(s) are configured in a repeating fractal pattern, in order to improve gas utilization within a bioreactor and reduce energy requirements.

BACKGROUND OF THE INVENTION

Ethanol is rapidly becoming a major hydrogen-rich liquid transport fuel around the world. Worldwide consumption of ethanol in 2005 was an estimated 12.2 billion gallons. The global market for the fuel ethanol industry has also been predicted to grow sharply in future, due to an increased interest in ethanol in Europe, Japan, the USA, and several developing nations.

For example, in the USA, ethanol is used to produce E10, a 10% mixture of ethanol in gasoline. In E10 blends the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, and as a pure fuel in its own right. Also, in Europe, environmental concerns surrounding the consequences of Green House Gas (GHG) emissions have been the stimulus for the European Union (EU) to set member nations a mandated target for the consumption of sustainable transport fuels such as biomass derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feed stocks is influenced by their value as human food or animal feed, while the cultivation of starch or sucrose-producing crops for ethanol production is not economically sustainable in all geographies. Therefore, it is of interest to develop technologies to convert lower cost and/or more abundant carbon resources into fuel ethanol.

CO is a major, free, energy-rich by-product of the incomplete combustion of organic materials such as coal or oil and oil derived products. For example, the steel industry in Australia is reported to produce and release into the atmosphere over 500,000 tonnes of CO annually.

Catalytic processes may be used to convert gases consisting primarily of CO and/or CO and hydrogen ($H_2$) into a variety of fuels and chemicals. Micro-organisms may also be used to convert these gases into fuels and chemicals. These biological processes, although generally slower than chemical reactions, have several advantages over catalytic processes, including higher specificity, higher yields, lower energy costs and greater resistance to poisoning.

The ability of micro-organisms to grow on CO as a sole carbon source was first discovered in 1903. This was later determined to be a property of organisms that use the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic and acetogenic organisms have been shown to metabolize CO to various end products, namely $CO_2$, $H_2$, methane, n-butanol, acetate and ethanol. While using CO as the sole carbon source, all such organisms produce at least two of these end products.

Anaerobic bacteria, such as those from the genus *Clostridium*, have been demonstrated to produce ethanol from CO, $CO_2$ and $H_2$ via the acetyl CoA biochemical pathway. For example, various strains of *Clostridium Ijungdahlii* that produce ethanol from gases are described in WO 00/68407, EP 1117309, U.S. Pat. Nos. 5,173,429; 5,593,886; and 6,368,819, WO 98/00558, and WO 02/08438. The bacterium *Clostridium autoethanogenum* sp is also known to produce ethanol from gases (Abrini et al., ARCHIVES OF MICROBIOLOGY 161, pp 345-351 (1994)).

However, ethanol production by micro-organisms by fermentation of gases is always associated with co-production of acetate and/or acetic acid. As some of the available carbon is converted into acetate/acetic acid rather than ethanol, the efficiency of production of ethanol using such fermentation processes may be less than desirable. Also, unless the acetate/acetic acid by-product can be used for some other purpose, it may pose a waste disposal problem. Acetate/acetic acid is converted to methane by micro-organisms and therefore has the potential to contribute to GHG emissions.

Microbial fermentation of CO in the presence of $H_2$ can lead to substantially complete carbon transfer into an alcohol. However, in the absence of sufficient $H_2$, some of the CO is converted into alcohol, while a significant portion is converted to $CO_2$ as shown in the following equations:

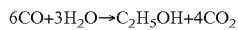

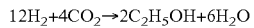

The production of $CO_2$ represents inefficiency in overall carbon capture and if released, also has the potential to contribute to Green House Gas emissions.

WO2007/117157, the disclosure of which is incorporated herein by reference, describes a process that produces alcohols, particularly ethanol, by anaerobic fermentation of gases containing carbon monoxide. Acetate produced as a by-product of the fermentation process is converted into hydrogen gas and carbon dioxide gas, either or both of which may be used in the anaerobic fermentation process. WO2008/115080, the disclosure of which is incorporated herein by reference, describes a process for the production of alcohol(s) in multiple fermentation stages. By-products produced as a result of anaerobic fermentation of gas(es) in a first bioreactor can be used to produce products in a second bioreactor. Furthermore, by-products of the second fermentation stage can be recycled to the first bioreactor to produce products.

U.S. Pat. No. 7,078,201 and WO 02/08438 also describe improving fermentation processes for producing ethanol by varying conditions (e.g., pH and redox potential) of the liquid nutrient medium in which the fermentation is performed. As disclosed in those publications, similar processes may be used to produce other alcohols, such as butanol.

Fermentation of gaseous substrates can be challenging due to the requirement that at least a portion of the gaseous substrate is dissolved in a typically aqueous fermentation broth before the substrate can be metabolised by a microbial culture. Fermentations involving gaseous substrates, wherein one or more gaseous components are the carbon and optionally the energy source for a microorganism, are particularly challenging due to the large amount of substrate required to be solubilised in a fermentation broth before any metabolism can take place. Examples of gaseous substrates used as a carbon and/or energy source in fermentation include CO, $CO_2$, $CH_4$, $H_2$ and $H_2S$. In particular, sparingly soluble substrates, such as CO and/or $H_2$ require highly efficient mass transfer into an aqueous fermentation broth as CO is both a carbon and energy source for anaerobic fermentation. For example, the theoretical equations for CO and $H_2$ to ethanol are:

$$6CO + 12H_2 \rightarrow 3C_2H_5OH + 3H_2O$$

Thus, six molecules of gas (CO and/or $H_2$) must be dissolved in a fermentation broth to produce one molecule of ethanol.

Mass transfer of a gas into a liquid is a function of three main variables:
1. Concentration Driving Force: The partial pressure of a particular gaseous component is substantially proportional to the rate at which that component can be driven into a solution.
2. Interfacial Surface Area: The larger the interfacial surface area between gas and liquid phases, the higher the opportunity for mass transfer. In particular, the interfacial surface area is typically a function of gas hold-up and bubble size.
3. Transfer Coefficient: The transfer coefficient of a system is influenced by a variety of factors. However, from a practical perspective, typically the largest influence is the relative velocity between the liquid and the gas phases. Relative velocities (and hence mass transfer) are typically increased by increasing turbulence through agitation or other mixing.

Various devices for the modification of fluid flow, e.g., to enhance mixing and/or otherwise improve control of multiphase (gas-liquid) processes are described in U.S. Pat. No. 6,333,019; U.S. Pat. No. 6,742,924; WO 2009/124939; and WO 2012/042245. In the case of processes for fermentation of gaseous substrates the efficient mass transfer of the gas into solution is only one of several variables affecting the degree of gas utilization or consumption by the bacterial culture. For example, once the gaseous feedstock is dissolved, it must be retained in the culture for a sufficient time for transfer to, and consumption by, the microbes. Both the energy input for circulating the liquid culture medium (e.g., in a loop from an upper section of a riser, back to a lower section near the gaseous feed inlet) in combination with the particular choice of equipment, are important considerations affecting CO utilization in two-phase biological fermentation processes, and consequently their overall economic viability. In this regard, mixing or gas-liquid contacting devices used conventionally to enhance gas-liquid mass transfer typically require large amounts of energy in order to attain the desired results in terms of overall CO utilization. To achieve effective fermentation of CO and optionally $H_2$ into products, such as acid(s) and alcohol(s), the CO-containing substrate must be not only dissolved, but also made available to the microorganisms in an efficient manner. Mechanical means, such as vigorous stirring, used conventionally for mass transfer improvement alone, often do not provide acceptable process economics in biological fermentation processes, as they require a large power input, which becomes inefficient and/or uneconomical as scale increases.

Even minor improvements to a fermentation process for producing one or more acids and/or one or more alcohols can have a significant impact on the efficiency, and more particularly, the commercial viability, of such a process. The present invention relates to system(s) and/or method(s) that overcome disadvantages known in the art and provide novel solutions for the optimal production of a variety of useful products.

SUMMARY OF THE INVENTION

In a first aspect, there is provided a bioreactor system for fermentation of a gaseous substrate to one or more products, the system including:
(a) a bioreactor containing a liquid nutrient media (or culture medium);
(b) at least one gas inlet configured to, in use, direct gaseous substrate (e.g., a CO-containing substrate) into the bioreactor;
(c) at least one perforated plate adapted to facilitate transfer of gaseous substrate into the liquid of the bioreactor; and
(d) at least one gas outlet, configured to, in use, allow gas to exit the reactor (e.g., following its disengagement from liquid culture medium at an upper section of a riser).

In a particular embodiment, the perforated plate may comprise a plurality of apertures configured in a repeating fractal pattern.

In a second aspect, there is provided a perforated plate, said plate comprising a plurality of apertures configured in a repeating fractal pattern to facilitate the mass transfer of the gas substrate to a liquid phase in a reactor.

In particular embodiments of the first and second aspects, the bioreactor is configured for fermentation of a gaseous substrate to produce products including acid(s) and/or alcohol(s). In a particular embodiment, the gaseous substrate comprises CO and optionally $H_2$. In alternative embodiments, the gaseous substrate comprises $CO_2$ and $H_2$.

In particular embodiments, at least one perforated plate, which may be positioned at the lowest axial height relative to other perforated plates in the bioreactor, is situated above the gas inlet configured to direct gaseous substrate into the bioreactor. In further embodiments, one or more, and preferably all, of the perforated plates substantially cover cross-sections (with the exception of open areas defined by apertures) of the bioreactor vessel above the gas inlet, for example, circular cross-sections in a riser. In accordance with the invention, the perforated plates provide turbulent mixing of the gaseous substrate, provided by the gas inlet into the liquid nutrient media of the bioreactor.

In particular embodiments, a series of at least two perforated plates are situated at different axial heights within the bioreactor (e.g., in a riser section thereof), each plate substantially covering a cross-section of the bioreactor. In further embodiments, the plates are situated at varying distances (e.g., axial heights) from one another within the bioreactor. In particular embodiments, the plates are situated at substantially equal distances (e.g., axial heights) from one another within the bioreactor.

In particular embodiments, the apertures of the plate(s) are configured in a fractal pattern of squares that lie orthogonally to the direction of the gas and liquid flow. In particular embodiments, the apertures of the plate(s) are configured in a fractal pattern of two or more sets of squares at two or more scales. In accordance with the invention, the solid surface portion of the plates is a surface which presents an obstruction to the oncoming fluid. This obstruction forces the fluid to pass through the apertures of the plate, effectively creating turbulence by modifying the fluid flow. The solid surface portion may include closed, elongated elements between the scales, i.e., referring to the sets of squares at a given scale. The closed, elongated elements may have different widths to thereby separate the sets of squares, or apertures having other shapes, at different scales by different distances.

In alternative embodiments to those described above, the apertures of the plate(s) are configured in a fractal pattern comprising geometric shapes other than squares. As would be understood by a skilled person, the apertures of the plates can be configured by two or more sets of any shape at two or more scales. As noted above with respect to square shapes, any other shapes may be separated at different scales by closed, elongated elements between the scales, at different widths, with each width of separation corresponding to a given scale. According to one embodiment, successively larger scales may be separated by successively greater widths. In certain embodiments a combination of different shapes can be used. In a particular embodiment, the perforations comprise repetitions of fractal geometric shapes that provide a plurality of internal and external edges and/or vertices that substantially disrupt the flow of gas and liquid passing through the aperture. The plurality of edges and/or vertices generated by the fractal repetitions provide additional sites for potential breakage of gas bubbles which improves mass transfer of the gaseous substrate to the liquid nutrient media.

In particular embodiments, the bioreactor is used for the fermentation of gaseous substrates comprising CO and optionally $H_2$ to produce products including ethanol, acetic acid, 2,3-butanediol, butanol, iso-propanol and acetone. Typically, the microbial fermentation of such substrates is carried out in liquid nutrient media by carboxydotrophic bacteria, such as *Clostridium autoethanogenum*. In particular embodiments, the fermentation is conducted by micro-organisms suspended in the liquid nutrient media. However, in particular embodiments, the micro-organisms can form a biofilm on the plate, particularly in the apertures of the plate.

In a third aspect, there is provided a method of improving mass transfer of a gaseous substrate to a liquid in a reactor, the method comprising passing the gaseous substrate and liquid through at least one perforated plate within the reactor, said perforated plate comprising a plurality of apertures configured as described herein, e.g., in a repeating fractal pattern.

In a fourth aspect, there is provided a method of fermentation of gaseous substrates to produce one or more products, comprising:
  (a) providing a gaseous substrate to a bioreactor comprising at least (i) a culture of one or more microorganisms; (ii) a liquid nutrient media; and (iii) at least one perforated plate adapted to facilitate transfer of gaseous substrate into the liquid of the bioreactor; and
  (b) fermenting the culture in the bioreactor to produce one or more products from said substrate.

In a fifth aspect, there is provided a method of producing products including acid(s) and/or alcohol(s) by fermentation of a gaseous substrate, the method comprising:
  (a) providing the gaseous substrate to a bioreactor comprising at least (i) a culture of one or more microorganisms; (ii) a liquid nutrient media; and (iii) at least one perforated plate adapted to facilitate transfer of gaseous substrate into the liquid of the bioreactor, wherein said perforated plate comprises a plurality of apertures configured in a repeating fractal pattern; and
  (b) anaerobically fermenting the culture in the bioreactor to produce one or more products including one or more acid(s) and/or alcohol(s) from said substrate.

In particular embodiments of the third, fourth and fifth aspects, the perforated plates are situated in the bioreactor and configured as described in the first and second aspects. In particular embodiments, the method comprises passing the gaseous substrate and liquid through the apertures of at least one perforated plate. In particular embodiments, the method comprises passing the gaseous substrate and liquid through a series of perforated plates.

Other embodiments of the invention relate to biological processes for converting carbon monoxide (CO) to an end product (e.g., a desired product such as ethanol) and optionally other metabolites. Representative processes comprise feeding a CO-containing substrate to a bioreactor containing carboxydotrophic bacteria in a liquid culture medium, to convert CO in the substrate to the end product, wherein the CO-containing substrate and liquid culture medium flow through apertures in a plurality of perforated plates. The apertures provide a total open area of at least about 20% of the surface area of their respective plates, and at least some of the apertures provide two or more vertices for enhancing CO utilization by the carboxydotrophic bacteria.

Yet further embodiments of the invention relate to bioreactor systems for converting carbon monoxide (CO) into a desired end product (e.g., a desired product such as ethanol) and optionally other metabolites. Representative systems comprise a bioreactor including a riser section for contacting a CO-containing, gaseous substrate with carboxydotrophic bacteria in a liquid culture medium. The riser section has a plurality of perforated plates arranged therein, with apertures in the perforated plates providing a total open area of at least about 20% (e.g., from about 20% to about 50%) of the surface area of their respective plates, and with at least some of the apertures providing two or more vertices for enhancing CO utilization by the carboxydotrophic bacteria. An outlet port above a top, perforated plate of the plurality of perforated plates (e.g., the top plate being disposed in the riser section at the highest axial height, relative to the other plates) is configured to allow gases to exit the bioreactor. In addition, a recirculation loop is configured to return liquid culture medium from above the top plate to a lower section of the bioreactor (e.g., the lower section corresponding to an axial height that is below a bottom plate, disposed in the riser section at the lowest axial height, relative to the other plates).

In particular embodiments, the one or more micro-organisms ferment a carbon containing substrate to produces products including acid(s) and alcohol(s) (e.g., a desired end product such as ethanol and other metabolites such as acetic acid). In certain embodiments, the one or more microorganisms produce one or more products by fermentation of a gaseous substrate comprising CO. In certain embodiments the fermentation is an anaerobic fermentation. In particular embodiments, the one or more micro-organism cultures convert CO and optionally $H_2$ to products including acid(s) and/or alcohol(s). In certain embodiments the products are selected from the group comprising ethanol, acetic acid, 2,3-butanediol, butanol, lactate, succinate, methyl ethyl ketone (MEK), propanediol, 2-propanol, isopropanol acetoin, iso-butanol, citramalate, butadiene, poly lactic acid, isobutylene, 3-hydroxy propionate (3HP), acetone and fatty acids.

In various embodiments, the fermentation is carried out using a microorganism culture comprising one or more strains of carboxydotrophic bacteria. In various embodiments, the carboxydotrophic bacterium is selected from *Clostridium, Moorella, Oxobacter, Peptostreptococcus,*

Acetobacterium, Eubacterium, or Butyribacterium. In one embodiment, the carboxydotrophic bacterium is Clostridium autoethanogenum. In a particular embodiment, the bacterium has the identifying characteristics of accession number DSMZ10061 or DSMZ23693.

The gaseous substrate may comprise a gas obtained as a by-product of an industrial process. In certain embodiments, the industrial process is selected from the group consisting of ferrous metal products manufacturing, non-ferrous products manufacturing, Refinery processes, petroleum refining processes, biofuel production processes (e.g., pyrolysis processes and fatty acid/triglyceride hydroconversion processes) gasification of biomass, gasification of coal, electric power production, carbon black production, ammonia production, methanol production and coke manufacturing. Alternatively, the gaseous substrate is a reformed gas from sources including natural gas, shale gas, associated petroleum gas and biogas. In alternative embodiments the gas is obtained by gasification of biomass or municipal solid waste. In one embodiment of the invention, the gaseous substrate is syngas. In one embodiment, the gaseous substrate comprises a gas obtained from a steel mill.

The invention also includes the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

These and other aspects and embodiments of the invention will become apparent from the following detailed description.

BRIEF DESCRIPTION OF THE DRAWINGS

A more complete understanding of the exemplary embodiments of the present invention and the advantages thereof may be acquired by referring to the following description in consideration of the accompanying Figures, in which the same reference numbers, or variations of the same reference numbers (e.g., 3 and 3a) are used to identify the same or similar features and wherein:

FIGS. 1-14 should be understood to present an illustration of the invention, principles involved, and/or specific experimental results achieved. A simplified process flow scheme is used in FIG. 1, in order to facilitate explanation and understanding. Details including heaters, valves, instrumentation, certain process lines such as for withdrawing liquid products, and other items not essential to the understanding of the invention are not shown. As is readily apparent to one of skill in the art having knowledge of the present disclosure, methods and associated equipment for carrying out biological conversion processes according to various other embodiments of the invention, will have configurations and components determined, in part, by their specific use.

DETAILED DESCRIPTION OF THE INVENTION

Definitions

Figure 1:
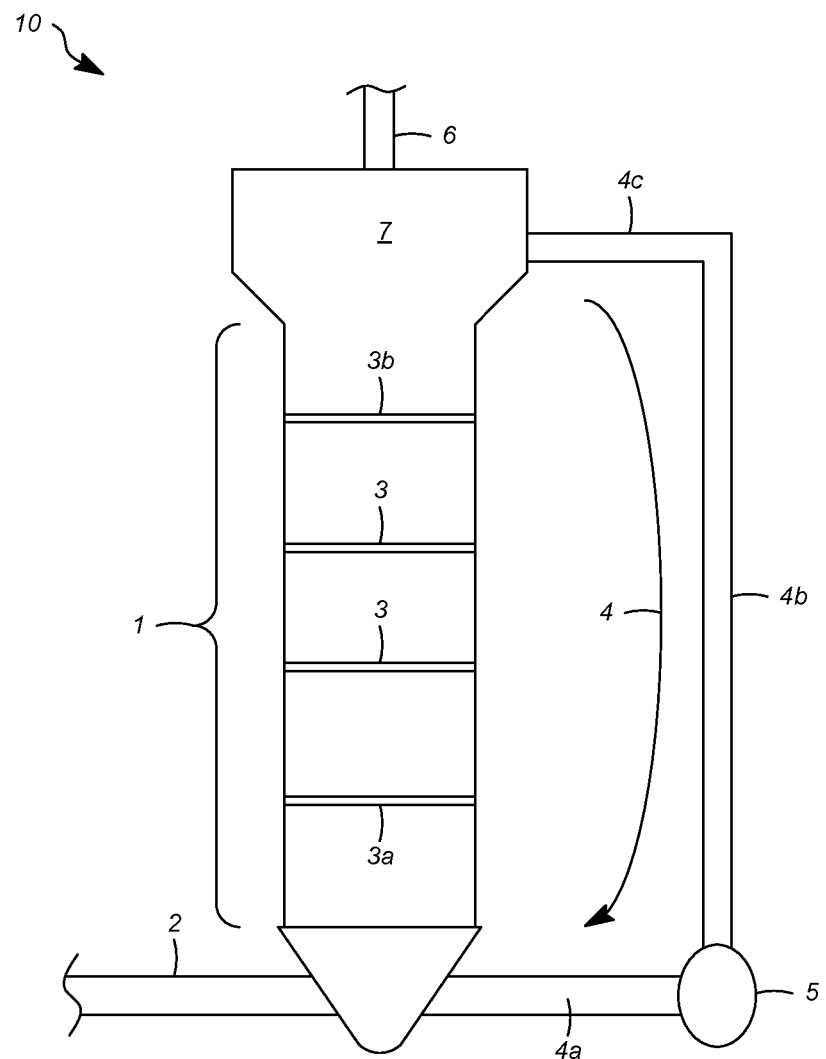
FIG. 1 shows an embodiment of the invention used for gas fermentation in a circulated liquid loop bioreactor.

Unless otherwise defined, the following terms as used throughout this specification are defined as follows:

The term "perforated plate" includes any substantially planar apparatus with a plurality of apertures on the surface. The plate may be formed of any suitable material, including metals and plastics. The apertures of the plate may be configured in a variety of shapes and sizes. Preferably, a plate has a circular cross section that is adapted to correspond to, or cover (except for open portions defined by apertures), cross-sectional areas within a bioreactor, for example a cylindrical riser section thereof. In general, a plate may have a thickness dimension that is significantly smaller than a radial or other width dimension (e.g., in the case of non-circular plates). For example, the thickness dimension is generally from about 0.1% to about 10%, typically from about 0.5% to about 7.5%, and often from about 1% to about 5% of the radial or width dimension.

The term "fractal pattern" and/or "fractal configuration" as used herein means a geometric pattern that is repeated and has a degree of self-similarity at a range of scales. The terms may also be taken to mean a shape or design with a fractal dimension that is a non-integer. The term fractal dimension is defined mathematically as:

fractal dimension=log(number of self-similar pieces)/log(magnification factor)

A fractal pattern may have complex or detailed structure at varying scales and/or irregularity both locally and globally.

The term "gaseous substrate" includes any gas which contains a compound or element used by a microorganism as a carbon source and optionally energy source in fermentation. The gaseous substrate, for example a "CO-containing substrate," will typically contain a significant proportion of CO, generally from about 5% to about 100%, typically from about 30% to about 95%, and often from about 50% to about 90% CO by volume, when introduced to the bioreactor. A CO-containing substrate may be subjected to any of a number of purification steps upstream of the bioreactor, in order to, for example, (i) increase the concentration of CO, (ii) decrease the concentration gases other than CO, and/or (iii) remove any gaseous, liquid, and/or solid impurities that may be detrimental to the biological conversion process and particularly to the bacteria used.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approximately 2:1, or 1:1, or 1:2 ratio of $H_2$:CO. In one embodiment the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of Hz, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In one embodiment the substrate comprises less than or equal to about 20% $CO_2$ by volume. In particular embodiments the substrate comprises less than or equal to about 15% $CO_2$ by volume, less than or equal to about 10% $CO_2$ by volume, less than or equal to about 5% $CO_2$ by volume or substantially no $CO_2$.

The terms "liquid nutrient media" and "culture medium" include a liquid medium comprising nutrients suitable for one or more microorganisms used to carry out fermentation. The liquid nutrient media will contain vitamins and/or minerals sufficient to permit growth of the micro-organism(s) used. Anaerobic media suitable for fermentation using CO are known in the art. For example, suitable media are described in Beibel (2001).

The term "bioreactor" includes devices and vessels for gas/liquid contact, suitable for conducting a desired fermentation.

The term "mass transfer" as used herein relates to the transfer of atoms or molecules, particularly substrate atoms or molecules from a gaseous phase into an aqueous solution.

The term "biofilm" relates to an aggregation of one or more microorganism(s) adhered to a surface.

The term "acid" as used herein includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. In addition, the term "acetate" includes both acetate salt alone and a mixture of molecular or free acetic acid and acetate salt, such as the mixture of acetate salt and free acetic acid present in a fermentation broth as described herein.

The terms "improving the efficiency", "increasing the efficiency" and the like, when used in relation to a fermentation process, include, but are not limited to, increasing one or more of the rate of growth of microorganisms catalyzing the fermentation, the growth and/or product production rate at elevated product concentrations, the volume of desired product produced per volume of substrate consumed, the rate of production or level of production of the desired product, and the relative proportion of the desired product (e.g., ethanol) produced compared with other by-products (e.g., other metabolites such as acetic acid) of the fermentation.

Unless the context requires otherwise, the phrases "fermenting", "fermentation process" or "fermentation reaction" and the like, as used herein, are intended to encompass both the growth phase and product biosynthesis phase of the process.

Particular aspects of the invention are associated with the discovery of certain types of internal structures (e.g., perforated plates as described herein), that, when used in biological processes for the conversion of CO to desired end products such as ethanol, can significantly enhance CO utilization by bacteria to commercially acceptable levels, and preferably without requiring an increased energy input. As noted above, the efficient mass transfer of CO into the liquid culture medium is only one of several variables affecting CO utilization or consumption by the bacterial culture. Once the CO and/or other gases in the feedstock (or CO-containing substrate) are dissolved, the gas(es) must be retained in the culture for a sufficient time for transfer to, and consumption by, the microbes. Both the energy input for circulating the liquid culture medium (e.g., in a loop from an upper section of a riser, back to a lower section near the gaseous feed inlet) in combination with the particular choice of equipment, are important considerations affecting CO utilization in two-phase biological fermentation processes, and consequently the overall economic viability of such processes. In this regard, conventional mixing or gas-liquid contacting devices for enhancing gas-liquid mass transfer, such as structured packing materials (rings, saddles, coils, etc.), static mixers, and other devices require increased energy for moving fluids through these devices with sufficient force, velocity, and/or turbulence to obtain adequate gas-liquid contacting performance. Therefore, the needed improvements in gas-liquid mass transfer associated with conventional devices, even if such improvements ultimately increase CO utilization in a given biological conversion process, are not necessarily economical or even advantageous, if the associated energy requirements are excessive.

Further impacting the desired objective of increasing CO utilization is the distribution of the bacteria itself, within the bioreactor. Different structures provide different surface geometries for both bacterial growth (e.g., in the form of a surface biofilm) and contact between CO (e.g., at the point at which it is solubilized in the culture medium) at the bacteria. Representative perforated plates as described herein provide a combination of structural features that significantly enhance CO utilization, preferably without added costs in terms of the energy required for circulation of the bacterial culture medium. These advantages result from a number of important performance parameters associated with biological conversion processes, and particularly those that involve gas-liquid contacting.

Conventional mixing or gas-liquid contacting devices used for mass transfer of a gas phase to a liquid phase, such as static mixers and others as described above, can require the gas to be injected into the liquid at high pressure. Other mixing methods, such mechanical stirring, require high energy in order to attain necessary mass transfer. An important performance advantage of the perforated plates as described herein is their ability to improve mass transfer of gas into liquid, particularly in instances where the gas is provided to the liquid medium at substantially reduced pressure (i.e., lower gas flow rates), such as in a system for fermentation of industrial waste gas, without the need for additional high energy mixing devices. By improving mass transfer of the gas, it is considered that elevated growth and/or metabolite production rates of the microorganisms can be achieved and/or the overall power usage is reduced compared to conventional fermentation processes. Importantly, the advantages described herein, in terms of improved CO utilization and/or decreased circulation energy requirements, can be realized in biological processes as described herein, which are carried out at a total pressure, or with a CO partial pressure of the CO-containing substrate at the point of entry into the bioreactor, of generally less than about 100 psig, typically less than about 50 psig, and often less than about 30 psig.

In view of the above considerations, in representative biological conversion processes, the CO utilization by the bacteria (e.g., carboxydotrophic bacteria) is enhanced by the use of perforated plates as described herein. The CO utilization refers to the percentage of CO that is input to the process (e.g., to the bioreactor, or to more than one bioreactor in the case of processes operating with multiple bioreactors) and utilized in the conversion to desired product(s) (e.g., ethanol) and other metabolites of the bacteria. If the amount and composition of the gas stream(s) exiting the process (e.g., one or more gas stream(s) withdrawn from one or more riser section(s) of one or more bioreactor(s)) are known, then the CO utilization may be calculated as:

1−(quantity of CO exiting the process)/(quantity of CO input to the process)

The CO utilization is determined on a "per pass" or "once-through" basis, without accounting for the use of gas recycle (and added expense) that can provide higher overall conversion levels. According to representative embodiments, the CO utilization by the bacteria is generally at least about 50% (e.g., from about 50% to about 95%), typically at least about 70% (e.g., from about 70% to about 95%), and often at least about 75% (e.g., from about 75% to about 90%). In some cases, CO utilization may be at least about 85%.

Importantly, as discussed above, aspects of the invention relate to the performance advantages obtained with one or more perforated plates, as described herein, in improving CO utilization in two-phase bacterial conversion processes, without added energy requirements, and associated costs, of increased circulation of liquid culture medium through the bioreactor. Therefore, according to particular embodiments, CO utilization is increased (e.g., to the levels as described above) in relation to the same biological process, or a reference biological process, without the use of the one or more perforated plates, and for example without the use of any gas-liquid contacting devices in place of the perforated plates (e.g., as in the case of an open riser without contacting devices). Preferably, the reference process, which is used as a basis for comparison of CO utilization, is a process in which all operating parameters (e.g., independently adjustable and controllable parameters such as pressure, temperature, flow rates, bacteria and metabolite concentrations, pH, etc.) are unchanged, including the energy input for circulation of the liquid culture medium (e.g., the loop pump energy input). According to particular embodiments, CO utilization by the bacteria is increased generally by at least about 5% (e.g., from about 5% to about 75%), typically by at least about 10% (e.g., from about 10% to about 50%), and often by at least about 15% (e.g., from about 15% to about 40%), relative to a reference biological process in which the perforated plates are not used and/or not replaced with other gas-liquid contacting devices. An increase in CO utilization refers to the absolute percentage increase (rather than a percentage of a percentage increase), whereby, for example, an increase from 45% CO utilization of a reference process to 60% CO utilization of a process using perforated plates as described herein, amounts to a 15% increase in CO utilization (i.e., 60%−45%). As will be appreciated by those skilled in the art, even a modest increase in CO utilization (e.g., on the order of several percent) provides a very significant economic advantage resulting from the more efficient utilization of the feedstock (or CO-containing substrate), for the same process energy requirements.

Conversely, other aspects of the invention relate to the reduction in energy requirements in biological conversion processes, as needed to achieve a given level of CO utilization. According to other representative embodiments, therefore, the energy input for circulation of the liquid culture medium (e.g., the loop pump energy input) may be reduced generally by at least about 20% (e.g., from about 20% to about 85%), typically by at least about 35% (e.g., from about 35% to about 80%), and often by at least about 50% (e.g., from about 50% to about 75%) in relation to the same biological process, or a reference biological process, without the use of the one or more perforated plates, and for example without the use of any gas-liquid contacting devices in place of the perforated plates (e.g., as in the case of an open riser without contacting devices). Preferably, the reference process in this case, which is used as a basis for comparison energy input requirements, is a process in which all operating parameters (e.g., independently adjustable and controllable parameters such as pressure, temperature, flow rates, bacteria and metabolite concentrations, pH, etc.) are unchanged, except that the energy input for circulation of the liquid culture medium (e.g., the loop pump energy input) is adjusted (e.g., increased) to match the CO utilization obtained in the inventive process utilizing one or more perforated plates as described herein.

The perforated plates, according to some embodiments, have been designed in such a way as to provide among other features, multiple surfaces that obstruct the flow of gas through the liquid medium in a bioreactor, and apertures with fractal patterned edges that provide a plurality of sites where gas bubbles may break and disperse into the liquid medium. The presence of the one or more perforated plates within the bioreactor thus provides a low-energy means for gas dispersion throughout the liquid medium. In certain embodiments, said perforated plates are utilized in a gas fermentation system comprising one or more microorganisms. Surprisingly, the inventors have identified that the use of said perforated plates in a bioreactor of a gas fermentation system significantly improves the gas utilization by the one or more microorganisms in the fermentation process, through the formation of a stable gas-in-liquid dispersion and/or other mechanisms as described herein.

In embodiments of the invention, the system has application in the fermentation of gaseous substrates to one or more products, said products including acids, alcohols and diols. In particular, ethanol, acetic acid and 2,3-butanediol are produced by fermentation of a gaseous substrate comprising CO.

The fermentation may be carried out in any suitable bioreactor, such as an immobilised cell reactor, a gas-lift reactor, a bubble column reactor (BCR), a membrane reactor, such as a Hollow Fibre Membrane Bioreactor (HFM BR) or a trickle bed reactor (TBR). Also, in some embodiments of the invention, the bioreactor may comprise a first growth reactor in which the micro-organisms are cultured, and a second, fermentation reactor, to which fermentation broth from the growth reactor may be fed and in which most of the fermentation product (e.g. ethanol and acetate) may be produced. The bioreactor of the present invention is adapted to receive a CO and/or Hz, or $CO_2$ and/or $H_2$ containing substrate.

In particular preferred embodiments, the perforated plates of the invention are installed in the riser of a circulated loop bioreactor. In such embodiments, the fermentation broth is circulated through a riser and downcomer portion of a bioreactor via a loop pump. It has been found by the inventors that the use of perforated plates comprising apertures configured in a repeating fractal pattern, or apertures having other features as described herein, are particularly advantageous in a circulated loop bioreactor, or other type of bioreactor in which a gaseous substrate is contacted with a liquid culture medium containing carboxydotrophic bacteria, under either co-current or counter-current flowing conditions, followed by separation of un-utilized gas(es) from the flowing culture medium. Compared to known mass transfer apparatuses, such as a static mixers, the perforated plates of the invention facilitate improved mass transfer and higher turbulence at reduced gas flow and/or liquid flow (e.g., obtained with a lower pump speed).

In particular embodiments, the fresh gas (e.g., the CO-containing substrate) is introduced into the reactor by one or more suitable gas inlets. Typically, high mass transfer rates can be achieved by introducing the gaseous substrate as fine bubbles. Those skilled in the art will appreciate means for introducing gaseous substrate, such as spargers. In particular embodiments, the gas is introduced into the vessel by fine bubble diffusers.

In alternative embodiments to those described above, the perforated plates are inserted into a pre-fermentation vessel, wherein the pre-fermentation vessel provides the fermentation reactor comprising one or more microorganism with a gas-saturated liquid. In such embodiments, the gaseous substrate is first provided to the pre-fermentation vessel comprising the perforated plates, wherein mass transfer of the gas to liquid substantially occurs, and the resulting gas-saturated liquid is subsequently passed to the fermentation reactor comprising one or more microorganisms for fermentation to one or more products. According to such embodiments, the "bioreactor" as described herein does not necessarily contain bacteria, but may instead contain the culture medium only, or may contain some other liquid, to be saturated with the gaseous feed and then introduced to a culture medium containing bacteria.

The perforated plates of the present invention are substantially planar. They may be of varying thickness, although they have thickness generally between 1-200 mm, and typically between 1-50 mm. In particular embodiments, the shape and diameter of the plate is dependent on the reactor on which it is to be inserted. Although not limited by material, the plates should comprise properties that are stable and corrosion-resistant. Suitable materials include metals, plastics or ceramics.

In embodiments of the invention, the apertures of the perforated plate are configured in a repeating fractal pattern. In particular embodiments, the apertures are arranged in a fractal pattern having at least three scales (e.g., from three to eight scales) of self-similarity. The scales may be separated by different distances, according to the widths of closed, elongated elements between the scales. The number of apertures present on the plate is not restrictive. Any shape that may be divided into smaller repeating units may be used in the invention, including, but not limited to, squares, rectangles, and triangles. In particular embodiments, the apertures are shaped as squares. In preferred embodiments, the apertures of the plate are configured in a repeating fractal pattern of four small squares within larger squares.

The multiple apertures of the perforated plate(s) may either be the same shape and size or of various shapes and sizes. In a particular embodiment, the apertures of the perforated plate are the same shape and size as each other. In an alternative embodiment, the apertures are each substantially the same shape but of different sizes on the plate. In a further alternative embodiment, the apertures are various different shapes and sizes.

In alternative embodiments of the invention, the apertures of the perforated plate comprise complex geometric designs. The apertures may be in the form of squares and/or slots, wherein the edges of the squares and/or slots comprise a plurality of vertices. The edges of the apertures may also comprise indentations and/or protrusions of shapes such as squares or triangles which provide additional vertices. When compared to standard geometric shapes, apertures with multiple vertices improve the mass transfer of the gas to the liquid medium by providing additional sites whereby larger gas bubbles may break and disperse into the liquid. In particular embodiments, the perforated plates comprise one or more slot apertures, said apertures comprising a plurality of vertices.

In embodiments of the invention, at least one perforated plate is situated within the bioreactor above, and orthogonal to, the gas inlet. The perforated plate substantially covers a cross section of the bioreactor above the gas inlet. The placement of at least one perforated plate above the gas inlet provides a flow guide which allows for highly efficient dispersion of the gas phase into liquid phase.

In particular embodiments, two or more perforated plates are situated at different heights within the bioreactor. The placement of two or more perforated plates within the bioreactor inherently creates a longer flow path for the liquid/gas medium to follow due to the series of flow restrictions the gas/liquid medium must overcome, resulting in a longer residence time. The gas entering the bioreactor is held up at each of the plates, creating separate stages within the bioreactor where the gas molecules may disperse through the liquid and be utilized by the microorganism, effectively increasing the interfacial surface area of the bioreactor.

In certain embodiments of the present invention, the bioreactor comprises a series of two of more perforated plates. In a preferred embodiment, the bioreactor comprises a series of at least three perforated plates, for example from three to 20 plates.

While two or more perforated plates of the present invention may be placed in a series within the bioreactor so that the apertures of the plates align with one another, it is advantageous that the apertures of the plates do not completely align. In particular embodiments, each plate in the series within the bioreactor, and consequently the pattern of apertures in a series of identical or similar plates, is axially rotated between substantially 40-90° to the preceding plate so that the apertures of adjacent plates do not align. In a preferred embodiment, each plate is axially rotated substantially 90° to the previous plate in the series. This increases the chance that gas or gas bubbles will come into contact with the surfaces of the plates or the edges of the plate's apertures, thereby increasing the gas hold up. Further, as the gas is forced to pass through the apertures of each plate in the series, the vertices, indentations and/or protrusions of the apertures agitate the gas and liquid flow. This provides an efficient means for turbulent mixing of the gas into the liquid medium, which may advantageously further increase the gas-liquid mass transfer coefficient. Without being bound by any particular theory, it is proposed that large and small eddies are produced from the fractal nature of the apertures, improving gas residence time in the bioreactor.

Separate perforated plates comprising apertures configured in two or more different fractal designs may be used in the bioreactor, such that adjacent perforated plates in the series comprises different aperture configurations. In certain embodiments, two plates comprising different aperture configurations are installed in an alternating arrangement within the bioreactor. In such embodiments, two axially adjacent plates in the series, while different in aperture configuration, are complementary to one another. Installed in this way, the majority of the aperture area of the first plate of a two-plate set aligns with the solid surface area of the adjacent, second plate of the set, increasing the likelihood that any given gas bubble will come into contact with an edge or surface as it flows through the liquid culture medium in the bioreactor. In various embodiments, the series of perforated plates within the bioreactor is comprised of two or more of said sets of complementary plates.

A surprising advantage of the use of the presently described perforated plates in a method of gas fermentation is increased CO utilization by the microorganism. Typical gas fermentation procedures involving traditional mixing techniques provide CO utilization by the microorganisms within the bioreactor of between 40-70%. In certain embodiments, a gas fermentation method comprising the perforated plates described herein provides CO utilization of between 70-95%. In further embodiments, the CO utilization is between 75-90%. In a preferred embodiment, the CO utilization is 80-85%.

While it is preferred that the perforated plates of the invention are used in a gas fermentation process, it will be appreciated that said plates may be used in the reactors of alternative chemical engineering processes requiring the mass transfer of a gas phase to a liquid phase, such as catalytic processes.

Various embodiments of systems of the invention are described in the accompanying Figures.

FIG. 1 is a schematic diagram of a circulated loop bioreactor comprising the perforated plates of the invention. In operation, microorganisms are cultured in a liquid fermentation broth, or culture medium, in bioreactor 10 and gaseous substrate can be introduced via gas inlet port 2. The gaseous substrate can be sparged into bioreactor 10 by any known sparging means. However, in particular embodiments, the gas is introduced through one or more fine bubble spargers or diffusers (not shown). In various embodiments, bioreactor 10 includes a series of perforated plates 3 arranged in a riser section 1 of bioreactor 10. According to the embodiment depicted in FIG. 1, the gaseous substrate is introduced through gas inlet port 2 below a bottom perforated plate 3a, which may have the lowest axial position in riser section 10, of perforated plates 3. In addition, fermentation broth is circulated around a downcomer portion 4b of recirculation loop section 4, using pump 5. The fermentation broth that is recycled in this manner can enter bioreactor 10 through recycle liquid inlet port 4a of recirculation loop section 4. Recycle inlet port 4a may be configured to introduce the recycled fermentation broth below bottom perforated plate 3a. Pump 5 may be any suitable liquid transfer device known in the art (e.g., a centrifugal pump) that causes the liquid culture medium to flow through riser section 1, together with the gaseous substrate, and particularly through apertures of perforated plates 3, with sufficient energy to achieve a desired degree of gas-liquid mass transfer, as described above.

Undissolved gases (e.g., un-utilized CO, impurities in the CO-containing substrate, and/or gaseous waste products of the fermentation), remaining after their residence time in riser section 1, may be separated from the liquid culture medium after flowing through apertures of top perforated plate 3b. Top perforated plate 3b may have the highest axial position in riser section 1, of perforated plates 3. This gas-liquid separation may occur in disengagement zone 7, having an expanded diameter. Undissolved gases exit through gas outlet port 6, which is above top perforated plate 3b. Liquid culture medium is returned through recirculation loop section 4. Specifically, liquid outlet port 4c of recirculation loop section 4 is configured to withdraw culture medium above top perforated plate 3b. Liquid culture medium is sent through downcomer portion 4b, and then to a lower section of the bioreactor, i.e., to below bottom perforated plate 3a, according to the embodiment depicted in FIG. 1.

Perforated plates 3 are therefore configured in horizontal or substantially horizontal planes, which are normal to the bulk, upward flows of both the CO-containing substrate and liquid culture medium in riser section 1. The upward flow of liquid culture medium in riser section 1 is induced by pump 5, whereas the upward flow of CO-containing substrate in this section is induced by its density difference, relative to the liquid culture medium.

Figure 2:
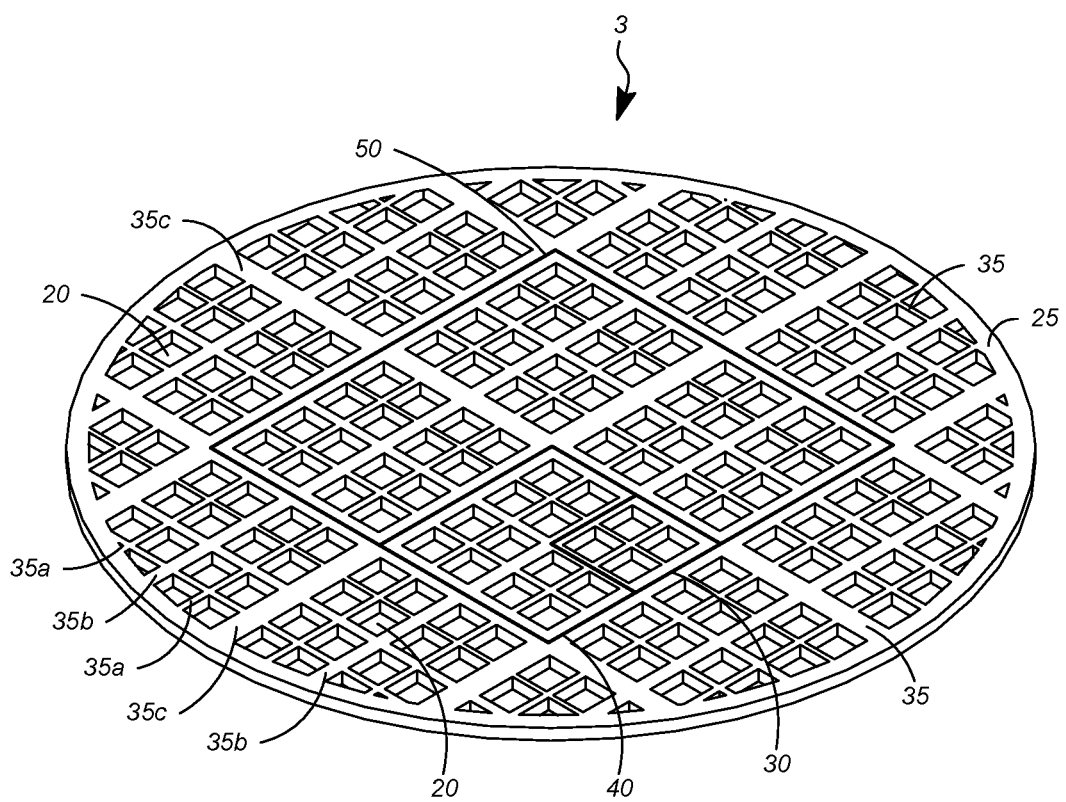
FIG. 2 shows an embodiment of the perforated plate of the invention comprising a square-in-square aperture configuration.

As discussed above, perforated plates 3 may comprise a plurality of apertures, which may be configured in a repeating fractal pattern. However, regardless of the exact geometry of the apertures, perforated plates 3 serve to effectively agitate the gas and liquid flowing through the bioreactor 10, and provide lengthened residence time of the gas within the liquid of the bioreactor 10 to improve mass transfer. In certain embodiments, each of the plurality of perforated plates 3 comprises apertures with the same fractal pattern (e.g., the same "square-in-square" fractal pattern as depicted in FIG. 2). In alternative embodiments, there are sets of two or more perforated plates 3, each plate in the set comprising apertures with different, complementary fractal patterns (e.g., the patterns of apertures depicted in FIGS. 3 and 4). In further alternative embodiments, each of the plurality of perforated plates 3 comprises apertures with different fractal patterns. The perforated plates 3 may be installed in the series so that the apertures of each plate align, or certain plates may be axially rotated so that the apertures do not align, which serves to provide greater gas hold up within bioreactor 10.

FIG. 2 depicts a representative perforated plate 3 with square-shaped apertures 20 arranged in a fractal pattern. Square-shaped apertures 20 may have a length (side) dimension of less than about 20 mm, less than about 10 mm, or even less than about 5 mm. The length dimension may be reduced to the smallest possible value that can be fabricated practically, for example using laser cutting or 3-D printing technology. Because the square aperture itself, or other shaped aperture (e.g., having edges and vertices as described herein), may provide the smallest scale of self-similarity of the fractal pattern, a reduction in the size of the aperture may allow for a greater number of scales of self-similarity to be used on a perforated plate of a given area. As shown in FIG. 2, in addition to square apertures 20 themselves providing a first scale, grouping 30 of four squares provides a square on a second scale, and grouping 40 of sixteen squares provides a square on a third scale, and grouping 50 of sixty-four squares provides a square on a fourth scale.

As is also apparent from the embodiment depicted in FIG. 2, perforated plate 3 includes a solid surface portion 25, which does not include apertures and provides an obstruction to gases and liquids flowing past perforated plate 3, thereby forcing these gases and liquids to take alternate paths through apertures 20. Solid surface portion 25 includes closed, elongated elements 35 or bars that separate apertures and, more specifically, separate the scales of apertures. For example, first elongated elements 35a of a first thickness (e.g., in the range from about 1 mm to about 20 mm) intersect at the center of grouping 30 of four squares (on the second scale). Second elongated elements 35b of a second thickness (e.g., in the range from about 2 mm to about 25 mm) that is greater than the thickness of first elongated elements 35a, intersect at the center of grouping 40 of sixteen squares (on the third scale). Third elongated elements 35c of a third thickness (e.g., in the range from about 3 mm to about 30 mm) that is greater than the thickness of second elongated elements 35b, intersect at the center of grouping 50 of sixty-four squares (on the fourth scale). In this manner, it can be seen that, for a given fractal pattern of apertures, the scales of self-similarity may be separated by different distances, for example according to widths of closed, elongated elements between the scales.

Figure 3:
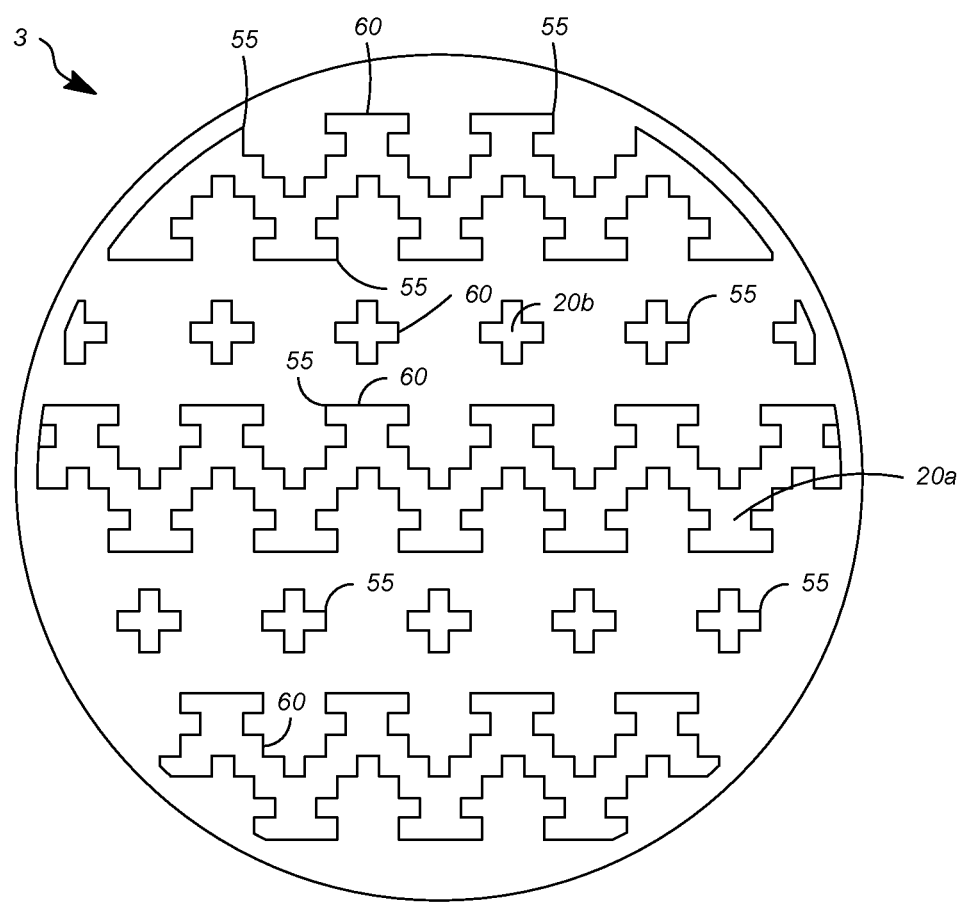
FIG. 3 shows an embodiment of a first complementary perforated plate of the invention comprising a first fractal design.
Figure 4:
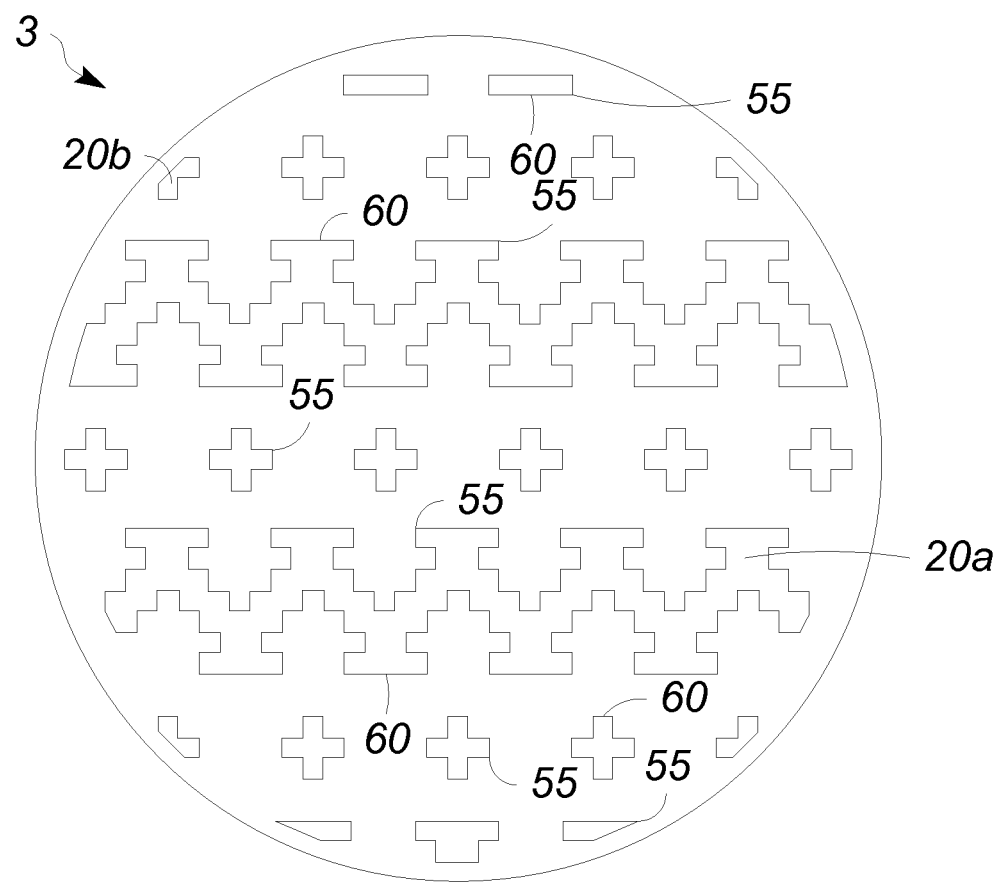
FIG. 4 shows an embodiment of a second complementary perforated plate of the invention comprising a second fractal design.

FIGS. 3 and 4 depict perforated plates 3 having both large and small apertures 20a, 20b with varying open areas and a plurality of vertices 55 formed by straight edges 60. In general, representative apertures can include at least three vertices (e.g., in the case of a triangular aperture) that may be formed by straight edges (e.g., intersecting at acute or right angles) or even curved edges. Vertices may number, for example, from 3 to 1000, depending on the detail with which apertures 20a, 20b may be fabricated. In general, a greater number of vertices promotes a greater degree of gas-liquid interaction near the surface of perforated plate 3, enhancing CO utilization by carboxydotrophic bacteria. Additional vertices, or surface features that may act in the same manner as vertices 20a, 20b in terms of their ability to break flowing gas bubbles, may be obtained by uneven or roughened edges, through abrasion of edges 60 during fabrication and/or coating of edges 60 with a rough surface coating. Such surface features may be imparted in lieu of forming further edges 60 and vertices 55 on a very fine scale, which may be prohibitive due to fabrication limitations.

As is apparent from FIGS. 3 and 4, large aperture(s) 20a, which may have the largest open area(s) of all apertures of perforated plate 3, can have an open area several times greater (e.g., at least three times greater, or at least five time greater) than the open area of small aperture(s) 20b, which may have the smallest open area(s) of all apertures of perforated plate 3. As is also apparent from FIGS. 3 and 4, aperture shapes of at least one perforated plate of the plurality of perforated plates 3 used in biological conversion processes described herein, can include a large number of edges, resulting in a large number of vertices. For example, one or more apertures (e.g., from about one to about 35 apertures) may have at least 10 vertices (e.g., from about 10 to about 200 vertices) and/or three or more apertures (e.g., from about three to about 20 apertures) may have at least 50 vertices (e.g., from about 50 to about 100 vertices). At least one aperture (e.g., from about one to about 20 apertures) of a given perforated plate may be formed predominantly by line segments having a length of less than about 20% (e.g., from about 1% to about 20%) of the perimeter of the aperture. Being formed "predominantly" in this regard means that at least 50% of the perimeter of the aperture is formed by such line segments. According to more specific embodiments, at least 80% (e.g., from about 80% to about 100%) of the perimeters of at least three apertures (e.g., from about three to about 10 apertures) of a given perforated plate may be formed predominantly by line segments having a length of less than about 10% (e.g., from about 1% to about 20%) of the perimeter of the aperture.

FIGS. 3 and 4, more specifically, illustrate an embodiment of a first complementary perforated plate comprising a first fractal design (FIG. 3) and a second complementary perforated plate comprising a second fractal design (FIG. 4). The two complementary perforated plate designs are inserted into the bioreactor, starting with either plate, such that they alternate in the series upstream of the gas inlet. The apertures of both plates comprise a plurality of vertices for bubble breakage, and are designed to increase the probability that gas bubbles that do not contact the vertices or the surface of the first plate in the series will contact the vertices or surface of the second plate in the series. The complementary aperture designs therefore optimize both hold up and bubble breakage of the gas in the liquid of the reactor.

Figure 5:
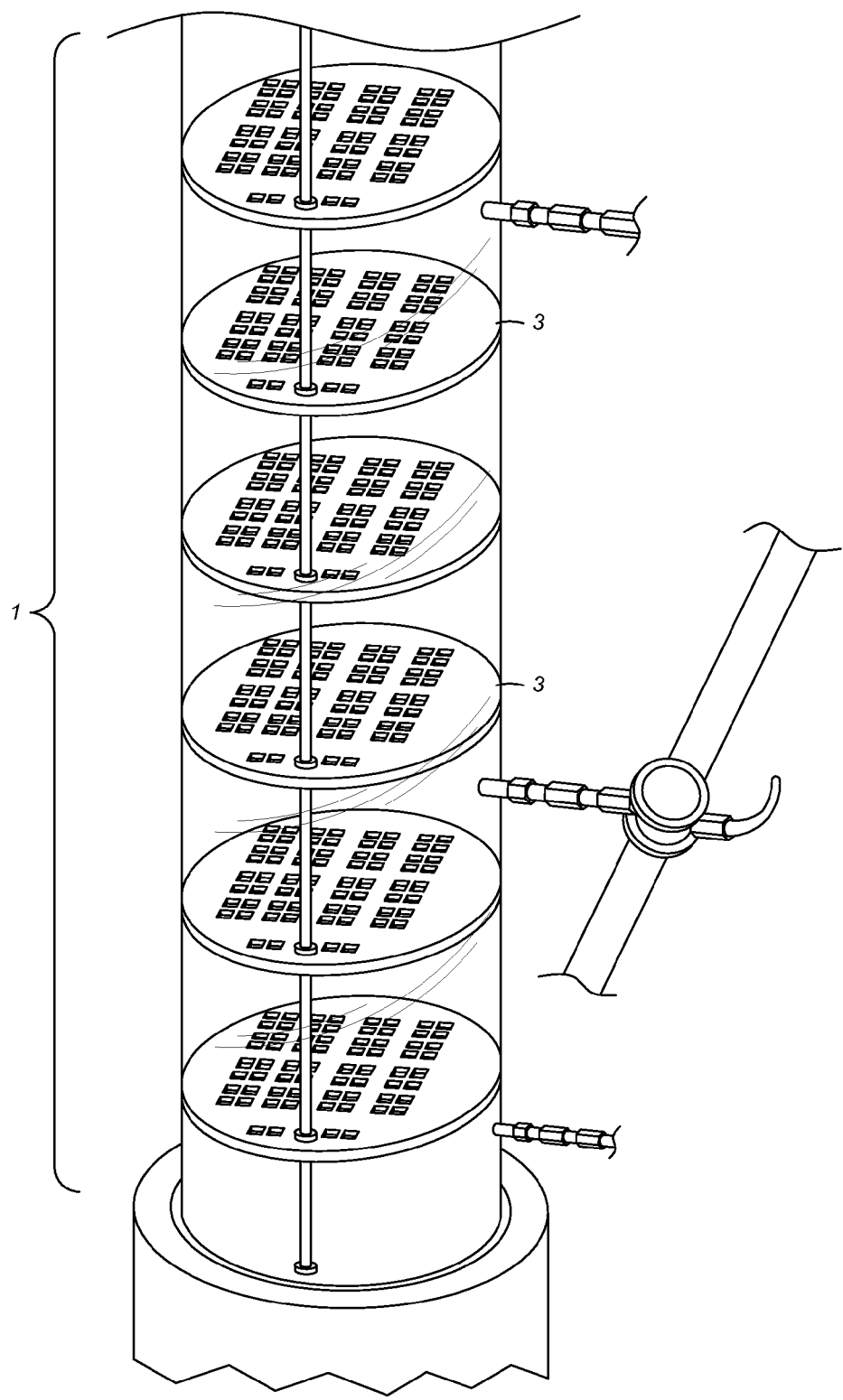
FIG. 5 shows an embodiment of the perforated plates of the invention installed within a column reactor.

FIG. 5 provides a close-up view of a series of perforated plates 3 arranged within a riser section 1 of a bioreactor. As described above, perforated plates 3 are arranged in substantially horizontal planes, normal to the bulk flows of CO-containing substrate and liquid culture medium. In general, at least three perforated plates (e.g., from three to 25 perforated plates) may be used, and more often at least five perforated plates (e.g., from five to 15 perforated plates) are used. In general, perforated plates may be spaced apart axially at regular axial intervals, i.e., at substantially the same axial distance, with this distance ranging, for example, from about 0.01 meters to about 1 meter, or from about 0.05 meters to about 0.5 meters.

Fermentation

Processes for the production of ethanol and other alcohols from gaseous substrates (such as those described in the Background section above) are known. Exemplary processes include those described, for example, in WO 2007/117157 and WO 2008/115080, as well as U.S. Pat. Nos. 6,340,581; 6,136,577; 5,593,886; 5,807,722; and 5,821,111, each of which is incorporated herein by reference.

A number of anaerobic bacteria are known to be capable of carrying out the fermentation of CO to alcohols, including n-butanol and ethanol, and acetic acid, and are suitable for use in the process of the present invention. Examples of such bacteria that are suitable for use in the invention include those of the genus *Clostridium*, such as strains of *Clostridium ljungdahlii*, including those described in WO 00/68407, EP 1117309, U.S. Pat. Nos. 5,173,429; 5,593,886; and 6,368,819; WO 98/00558 and WO 02/08438, *Clostridium carboxydivorans* (Liou et al., INTERNATIONAL JOURNAL OF SYSTEMATIC AND EVOLUTIONARY MICROBIOLOGY 33: pp 2085-2091) and *Clostridium autoethanogenum* (Abrini et al., ARCHIVES OF MICROBIOLOGY 161: pp 345-351). Other suitable bacteria include those of the genus *Moorella*, including *Moorella* sp HUC22-1 (Sakai et al., BIOTECHNOLOGY LETTERS 29: pp 1607-1612), and those of the genus *Carboxydothermus* (Svetlichny, V. A., et al. (1991), SYSTEMATIC AND APPLIED MICROBIOLOGY 14: 254-260). The disclosures of each of these publications are incorporated herein by reference. In addition, other carboxydotrophic anaerobic bacteria can be used in the processes of the invention by a person of skill in the art. It will also be appreciated upon consideration of the instant disclosure that a mixed culture of two or more bacteria may be used in processes of the present invention.

Culturing of the bacteria used in a method of the invention may be conducted using any number of processes known in the art for culturing and fermenting substrates using anaerobic bacteria. Exemplary techniques are provided in the "Examples" section below. By way of further example, those processes generally described in the following articles using gaseous substrates for fermentation may be utilized: (i) K. T. Klasson, et al. (1991). "*Bioreactors for synthesis gas fermentations resources.*" CONSERVATION AND RECYCLING, 5; 145-165; (ii) K. T. Klasson, et al. (1991). "*Bioreactor design for synthesis gas fermentations.*" FUEL. 70. 605-614; (iii) K. T. Klasson, et al. (1992). "*Bioconversion of synthesis gas into liquid or gaseous fuels.*" ENZYME AND MICROBIAL TECHNOLOGY. 14; 602-608; (iv) J. L. Vega, et al. (1989). "*Study of Gaseous Substrate Fermentation: Carbon Monoxide Conversion to Acetate. 2. Continuous Culture.*" BIOTECH. BIOENG. 34. 6. 785-793; (v) J. L. Vega, et al. (1989). "*Study of gaseous substrate fermentations: Carbon monoxide conversion to acetate. 1. Batch culture.*" BIOTECH. BIOENG. 34. 6. 774-784; (vi) J. L. Vega, et al. (1990). "Design of Bioreactors for Coal Synthesis Gas Fermentations." RESOURCES, CONSERVATION AND RECYCLING." 3. 149-160; all of which are incorporated herein by reference.

One exemplary micro-organism suitable for use in the present invention is *Clostridium autoethanogenum*. In one embodiment, the *Clostridium autoethanogenum* is a *Clostridium autoethanogenum* having the identifying characteristics of the strain deposited at the German Resource Center for Biological Material (DSMZ) under the identifying deposit number 19630. In another embodiment, the *Clostridium autoethanogenum* is a *Clostridium autoethanogenum* having the identifying characteristics of DSMZ deposit number DSMZ 10061.

The fermentation may be carried out in any suitable bioreactor. In some embodiments of the invention, the bioreactor may comprise two reactors in series, namely a first, growth reactor in which the micro-organisms are cultured, and a second, fermentation reactor, to which fermentation broth from the growth reactor is fed and in which most of the fermentation product (e.g., ethanol and acetate) is produced.

According to various embodiments of the invention, the carbon source for the fermentation reaction is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as is conducted in a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. In alternative embodiments, the CO-containing gas is a purpose-reformed gas from sources including natural gas, shale gas, associated petroleum gas and biogas. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

The CO-containing gaseous substrate will ideally contain a significant proportion of CO, such as at least 5% to about 100% CO by volume, or from 20% to 95% CO by volume, or from 40% to 95% CO by volume, or from 60% to 90% CO by volume or from 70% to 90% CO by volume. Gaseous substrates having lower concentrations of CO, such as 6% or less by volume, may also be appropriate, particularly when $H_2$ and $CO_2$ are also present.

While it is not necessary for the gaseous substrate to contain any hydrogen, the presence of hydrogen will generally not be detrimental to product formation in accordance with methods of the invention. However, in certain embodiments of the invention, the gaseous substrate is substantially hydrogen free (e.g., comprises less than 1% hydrogen by volume). The gaseous substrate may also contain some $CO_2$, such as about 1% to about 30% by volume, or such as about 5% to about 10% $CO_2$ by volume.

As noted previously, the presence of hydrogen in the substrate stream can lead to an improvement in efficiency of overall carbon capture and/or ethanol productivity. For example, WO0208438 describes the production of ethanol using gas streams of various compositions. In one preferred embodiment, a substrate stream comprising 63% $H_2$, 32% CO and 5% $CH_4$ was provided to a culture of *C. Ijungdahlii* in a bioreactor to promote microbial growth and ethanol production. When the culture reached a steady state and microbial growth was no longer the main objective, the substrate stream was switched to 15.8% $H_2$, 36.5% CO, 38.4% $N_2$ and 9.3% $CO_2$ in order to provide CO in a slight excess and promote ethanol production. This document also describes gas streams with higher and lower CO and $H_2$ concentrations.

Accordingly, it may be necessary to alter the composition of the substrate stream in order to improve alcohol production and/or overall carbon capture. Additionally or alternatively, the composition may be altered (i.e., CO, $CO_2$ and/or $H_2$ levels adjusted) to optimize the efficiency of the fermentation reaction and ultimately improve alcohol production and/or overall carbon capture.

In some embodiments, the CO-containing gaseous substrate may be sourced from the gasification of organic matter such as methane, ethane, propane, coal, natural gas, crude oil, low value residues from oil refinery (including petroleum coke or petcoke), solid municipal waste or biomass. Biomass includes by-products obtained during the extraction and processing of foodstuffs, such as sugar from sugarcane, or starch from maize or grains, or non-food biomass waste generated by the forestry industry. Any of these carbonaceous materials can be gasified, i.e., partially combusted with oxygen, to produce synthesis gas (syngas comprising significant amounts of $H_2$ and CO). Gasification processes typically produce a synthesis gas with a molar ratio of $H_2$ to CO of about 0.4:1 to 1.2:1, together with lesser amounts of $CO_2$, $H_2S$, methane and other inert substances. The ratio of the gas produced can be varied by means known in the art and are described in detail in WO2007/01616. However, by way of example, the following gasifier conditions can be altered to adjust the CO:$H_2$ product ratio: feedstock composition (particularly C:H ratio), operating pressure, temperature profile (influencing quench of product mix) and oxidant employed (air, oxygen enriched air, pure $O_2$ or steam, wherein steam tends to result in higher CO:$H_2$ ratios). Accordingly, the operating conditions of the gasifier can be adjusted to provide a substrate stream with a desirable composition for fermentation or blending with one or more other streams to provide an optimized or desirable composition for increased alcohol productivity and/or overall carbon capture in a fermentation process.

In other embodiments, the substrate comprising CO can be derived from the steam reforming of hydrocarbons. Hydrocarbons, such as natural gas hydrocarbons can be reformed at high temperature to yield CO and $H_2$ according to the following:

$$C_nH_m + nH_2O \rightarrow nCO + (m/2+n)H_2$$

By way of example, steam methane reforming involves reacting steam with methane to produce CO and $H_2$ at elevated temperature (700-1100° C.) in the presence of a nickel catalyst. The resulting stream (comprising 1 mol CO and 3 mol $H_2$ for every mol $CH_4$ converted) can be passed directly to the fermenter or blended with a substrate stream from another source to increase ethanol productivity and/or overall carbon capture in a fermentation process. Alcohols such as methanol can also be reformed to produce $CO_2$ and $H_2$ that may be used in a similar manner. Typically, the substrate streams used in the invention will be gaseous; however, the invention is not limited thereto. For example, the carbon monoxide may be provided to a bioreactor in a liquid. For example, a liquid may be saturated with a carbon monoxide containing gas and then that liquid added to a bioreactor. This may be achieved using standard methodology. By way of example, a microbubble dispersion generator (Hensirisak et al., "Scale-up of microbubble dispersion generator for aerobic fermentation," APPLIED BIOCHEMISTRY AND BIOTECHNOLOGY Volume 101, Number 3, October, 2002) could be used for this purpose.

It will be appreciated that for growth of the bacteria and CO-to-ethanol fermentation to occur, in addition to the CO-containing substrate gas, a suitable liquid nutrient medium will need to be fed to the bioreactor. A nutrient medium will contain vitamins and minerals sufficient to permit growth of the micro-organism used. Anaerobic media suitable for the fermentation of ethanol using CO as the sole carbon source are known in the art. For example, suitable media are described in U.S. Pat. Nos. 5,173,429 and 5,593,886 and WO 02/08438, WO2007/115157 and WO2008/115080, referred to above.

The fermentation should desirably be carried out under appropriate conditions for the desired fermentation to occur (e.g., CO-to-alcohol). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

The optimum reaction conditions will depend partly on the particular micro-organism used. However, in general, it may be preferable that the fermentation be performed at a pressure, or CO partial pressure, higher than ambient pressure. Operating at increased pressures allows a significant increase in the rate of CO transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

Also, because a given CO-to-ethanol conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e., bioreactors operated at 10 atmospheres of pressure need only be one tenth the volume of those operated at 1 atmosphere of pressure.

The benefits of conducting a gas-to-ethanol fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO-containing gaseous substrate is such as to ensure that the concentration of CO in the liquid phase does not become limiting. This is because a consequence of CO-limited conditions may be that the ethanol product is consumed by the culture.

Product Recovery

The products of the fermentation reaction can be recovered using known methods.

Exemplary methods include those described in WO2007/117157, WO2008/115080 and U.S. Pat. Nos. 6,340,581; 6,136,577; 5,593,886; 5,807,722; and 5,821,111. However, briefly and by way of example only, ethanol may be recovered from the fermentation broth by methods such as fractional distillation or evaporation, and extractive fermentation.

Distillation of ethanol from a fermentation broth yields an azeotropic mixture of ethanol and water (i.e., 95% ethanol and 5% water). Anhydrous ethanol can subsequently be obtained through the use of molecular sieve ethanol dehydration technology, which is also well known in the art.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. In this process, oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed, while the non-volatile oleyl alcohol is recovered for re-use in the fermentation.

Acetate may also be recovered from the fermentation broth using methods known in the art. For example, an adsorption system involving an activated charcoal filter may be used. In this case, microbial cells are typically first removed from the fermentation broth using a suitable separation method. Numerous filtration-based methods of generating a cell free fermentation broth for product recovery are known in the art. The cell free ethanol- and acetate-containing permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth be reduced to less than about 3 before it is passed through the activated charcoal column, to convert the majority of the acetate to the acetic acid form.

Acetic acid adsorbed to the activated charcoal may be recovered by elution using methods known in the art. For example, ethanol may be used to elute the bound acetate. In certain embodiments, ethanol produced by the fermentation process itself may be used to elute the acetate. Because the boiling point of ethanol is 78.8° C. and that of acetic acid is 107° C., ethanol and acetate can readily be separated from each other using a volatility-based method such as distillation.

Other methods for recovering acetate from a fermentation broth are known in the art and may be used in processes of the present invention. For example, U.S. Pat. Nos. 6,368,819 and 6,753,170 describe a solvent and cosolvent system that can be used for extraction of acetic acid from fermentation broths. As with the oleyl alcohol-based system described above for the extractive fermentation of ethanol, the systems described in U.S. Pat. Nos. 6,368,819 and 6,753,170 describe a water immiscible solvent/co-solvent that can be mixed with the fermentation broth in either the presence or absence of the fermented micro-organisms to extract the acetic acid. The solvent/co-solvent containing the acetic acid is then separated from the broth by distillation. A second distillation step may then be used to purify the acetic acid from the solvent/co-solvent system.

The products of the fermentation reaction (for example ethanol and acetate) may be recovered from the fermentation broth by continuously removing a portion of the broth from the fermentation bioreactor, separating microbial cells from the broth (conveniently by filtration), and recovering one or more products from the broth simultaneously or sequentially. Ethanol may conveniently be recovered by distillation, and acetate may be recovered by adsorption on activated charcoal, using the methods described above. The separated microbial cells can be returned to the fermentation bioreactor. The cell free permeate remaining after the ethanol and acetate have been removed can also be returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

Industrial Off Gas as a Resource for Fermentation

In accordance with other aspects of the invention, industrial waste gases are used in a fermentation reaction with no or only minimal additional scrubbing or pre-treatment steps being used to make the gases suitable therefor.

The waste gases may result from any number of industrial processes. The invention has particular applicability to supporting the production of ethanol from gaseous substrates such as high volume CO-containing industrial flue gases. Examples include gases produced during ferrous metal products manufacturing, non-ferrous products manufacturing, refinery processes, petroleum refining processes, gasification of coal, gasification of biomass, electric power production, carbon black production, ammonia production, methanol production and coke manufacturing. In certain embodiments the CO containing substrate is derived from gasification of biomass or municipal solid waste. In a particular embodiment of the invention, the waste gases are generated during a process for making steel. For example, those skilled in the art will appreciate the waste gases produced during various stages of the steel making process have high CO and/or $CO_2$ concentrations. In particular, the waste gas produced during the decarburization of steel in various methods of steel manufacturing, such as in an oxygen converter (e.g., BOF or KOBM), has a high CO content and low $O_2$ content making it a suitable substrate for anaerobic carboxydotrophic fermentation.

Waste gases produced during the carburization of steel are optionally passed through water to remove particulate matter before passing to a waste stack or flue for directing the waste gas into the atmosphere. Typically, the gases are driven into the waste stack with one or more fans.

In particular embodiments of the invention, at least a portion of the waste gas produced during the decarburization of steel is diverted to a fermentation system by suitable conduit means. By way of example, piping or other transfer means can be connected to the waste gas stack from a steel mill to divert at least a portion of the waste gas to a fermentation system. Again, one or more fans can be used to divert at least a portion of the waste gas into the fermentation system. In particular embodiments of the invention, the conduit means is adapted to provide at least a portion of the waste gas produced during the decarburization of steel to a fermentation system. The control of and means for feeding gases to a bioreactor will be readily apparent to those of ordinary skill in the art to which the invention relates.

While steel mills can be adapted to substantially continuously produce steel and subsequently waste gases, particular aspects of the process may be intermittent. Typically, the decarburization of steel is a batch process lasting several minutes to several hours. As such, the conduit means may be adapted to divert at least a portion of the waste gas, such as the gas produced during the decarburization of steel, to the fermentation system if it is determined the waste gas has a desirable composition.

The pH of the contents of the bioreactor used in the fermentation process may be adjusted as required. The appropriate pH will be dependent on the conditions required for a particular fermentation reaction having regard to the nutrient media and micro-organisms used, as will be appreciated by persons of ordinary skill in the art to which the invention relates. In one preferred embodiment, in fermentation of a gaseous substrate containing CO utilizing *Clostridium autoethanogenum*, the pH may be adjusted to approximately 5.5 to 6.5, most preferably to approximately 5.5. Further examples include pH 5.5 to 6.5 using *Moorella thermoacetica* for the production of acetic acid, pH 4.5 to 6.5 using *Clostridium acetobutylicum* for the production of butanol, and pH 7 using *Carboxydothermus hygrogenaformans* for the production of hydrogen. Those skilled in the art will be aware of suitable means for maintaining the bioreactor at the required pH. However, by way of example, aqueous bases such as NaOH and aqueous acids such as $H_2SO_4$ can be used to raise and lower the pH of the fermentation medium and maintain the desired pH.

Additional benefits of representative processes result from no or only minimal scrubbing and/or other treatment processes being performed on the waste gases prior to their use in a fermentation reaction. These gases will contain additional material resulting from the industrial process, which additional material may be used, at least in part, as a feedstock for the fermentation reaction.

General

Embodiments of the invention are described by way of example. However, it should be appreciated that particular steps or stages necessary in one embodiment may not be necessary in another. Conversely, steps or stages included in the description of a particular embodiment can be optionally advantageously utilized in embodiments where they are not specifically mentioned.

While the invention is broadly described with reference to any type of stream that may be moved through or around the system(s) by any known transfer means, in certain embodiments, the substrate and/or exhaust streams are gaseous. Those skilled in the art will appreciate that particular stages may be coupled by suitable conduit means or the like, configurable to receive or pass streams throughout a system. A pump or compressor may be provided to facilitate delivery of the streams to particular stages. Furthermore, a compressor can be used to increase the pressure of gas provided to one or more stages, for example the bioreactor. As discussed hereinabove, the pressure of gases within a bioreactor can affect the efficiency of the fermentation reaction performed therein. Thus, the pressure can be adjusted to improve the efficiency of the fermentation. Suitable pressures for common reactions are known in the art.

In addition, the systems or processes of the invention may optionally include means for regulating and/or controlling other parameters to improve overall efficiency of the process. One or more processors may be incorporated into the system to regulate and/or control particular parameters of the process. For example particular embodiments may include determining means to monitor the composition of substrate and/or exhaust stream(s). In addition, particular embodiments may include a means for controlling the delivery of substrate stream(s) to particular stages or elements within a particular system if the determining means determines the stream has a composition suitable for a particular stage. For example, in instances where a gaseous substrate stream contains low levels of CO or high levels of $O_2$ that may be detrimental to a fermentation reaction, the substrate stream may be diverted away from the bioreactor. In particular embodiments of the invention, the system includes means for monitoring and controlling the destination of a substrate stream and/or the flow rate, such that a stream with a desired or suitable composition can be delivered to a particular stage.

In addition, it may be necessary to heat or cool particular system components or substrate stream(s) prior to or during one or more stages in the process. In such instances, known heating or cooling means may be used. For example, heat exchangers may be employed to heat or cool the substrate streams.

Furthermore, the system may include one or more pre/post treatment steps to improve the operation or efficiency of a particular stage. For example, a pre-treatment step may include means for removing particulate matter and/or long chain hydrocarbons or tars from a gaseous substrate stream. Other pre- or post-operations that may be conducted include separation of desired product(s) from particular stages, such as, for example, the bioreactor production stage (e.g., removal of ethanol by distillation).

The invention has been described herein with reference to certain preferred embodiments, in order to enable the reader to practice the invention without undue experimentation. Those skilled in the art will appreciate that the invention can be practiced in a large number of variations and modifications other than those specifically described. It is to be understood that the invention includes all such variations and modifications. Furthermore, titles, headings, or the like are provided to aid the reader's comprehension of this document, and should not be read as limiting the scope of the present invention. The entire disclosures of all applications, patents and publications cited herein are herein incorporated by reference.

More particularly, as will be appreciated by one of skill in the art, implementations of embodiments of the invention may include one or more additional elements. Only those elements necessary to understand the invention in its various aspects may have been shown in a particular example or in the description. However, the scope of the invention is not limited to the embodiments described and includes systems and/or methods including one or more additional steps and/or one or more substituted steps, and/or systems and/or methods omitting one or more steps.

The reference to any prior art in this specification is not, and should not be taken as, an acknowledgement or any form of suggestion that that prior art forms part of the common general knowledge in the field of endeavor in any country.

Throughout this specification and any claims which follow, unless the context requires otherwise, the words "comprise", "comprising" and the like, are to be construed in an inclusive sense as opposed to an exclusive sense, that is to say, in the sense of "including, but not limited to."

EXAMPLES

The following examples are set forth as representative of the present invention. These examples are not to be construed as limiting the scope of the invention as these and other equivalent embodiments will be apparent in view of the present disclosure and appended claims.

Example 1

Comparison of Bioreactor Performance with Various Riser Internals

The effect of using differing reactor internal structures on performance parameters, including CO utilization, was evaluated for a biological process for converting CO to ethanol using an aqueous culture of *Clostridium autoethanogenum*. A circulated loop reactor was used for the studies, in which a CO-containing feed gas was sparged into the bacterial culture near the bottom of a riser section, and was allowed to dissolve in the liquid, such that it could be consumed in the bacterial fermentation for the production of ethanol and other metabolites (e.g., acetic acid or acetate). At the top of the riser, unconverted (i.e., un-utilized) CO and other gases in the feed, which were not dissolved or entrained in the bacterial culture, were disengaged from the liquid and exited the reactor at an outlet port above the riser section. A circulation pump ("loop pump") returned the liquid, free of the disengaged gas, back to the bottom of the riser, near the level of entry of the feed gas. The total liquid volume of the circulated loop reactor was about 15 liters. CO consumption, or utilization, by the bacteria was measured based on the difference between the amounts of CO supplied to the bioreactor and exiting in the gas removed from the reactor. Samples of culture medium, both containing bacteria (biomass) and also filtered to remove the bacteria, were analyzed periodically to determine the concentrations of ethanol and other metabolites, as well as that of the bacteria itself.

Three different internal riser configurations were tested in a series of batch runs. To the extent possible, reactor conditions were designed such that gas utilization was the only dependent variable, in order to provide an effective comparison of the tested internal structures. In this regard, emphasis was placed on maintaining similar metabolite profiles in the experiments, in order to rule out effects related to differing metabolite concentrations or stages of bacterial growth. The three internal riser configurations involved the use of (1) an open riser, i.e., no gas-liquid contacting structures or other reactor internals, (2) conventional static mixers, having multiple levels of angled plates, and (3) fractal grids, i.e., plates having apertures arranged in fractal pattern, namely a repeating pattern as seen in different scales of measurement. In the case of (2), four static mixer sections were spaced evenly in the riser, in order to test their effectiveness in the biological system, based on improving gas-liquid mixing and promoting even bubble distribution throughout. In the case of (3), eight fractal grids were spaced evenly apart at about 90 mm of axial height along the riser, according to the configuration illustrated in FIG. 5. The "square-in-square" fractal geometry of the grids (see FIG. 2) was tested for its ability to provide high turbulence at both shorter and longer dimensions, corresponding to different axial distances from the grids. The hole diameter of one square-shaped aperture of the grid was 3 mm.

A total of five batch biological conversion processes were performed using the riser internal configurations described above, and specifically two experiments using the open riser configuration, one experiment using the static mixers, and two experiments using the fractal grids. Details of these experiments are provided in the table below:

Batch Runs—Evaluation of Riser Internals

| Run | Riser Configuration | CO-Containing Gas Flow (l/min) | Loop Pump Speed (rpm) | Reactor Pressure (psi) |
|---|---|---|---|---|
| 1 | Open | 5.6 | 300 | 5 |
| 2 | Open | 5.6 | 380 | 5 |
| 3 | 4 Static Mixers | 5.6 | 300 | 5 |
| 4 | 8 Fractal Grids | 5 | 250 | 5 |
| 5 | 8 Fractal Grids | 3.6 | 380 | 5 |

Figure 6:
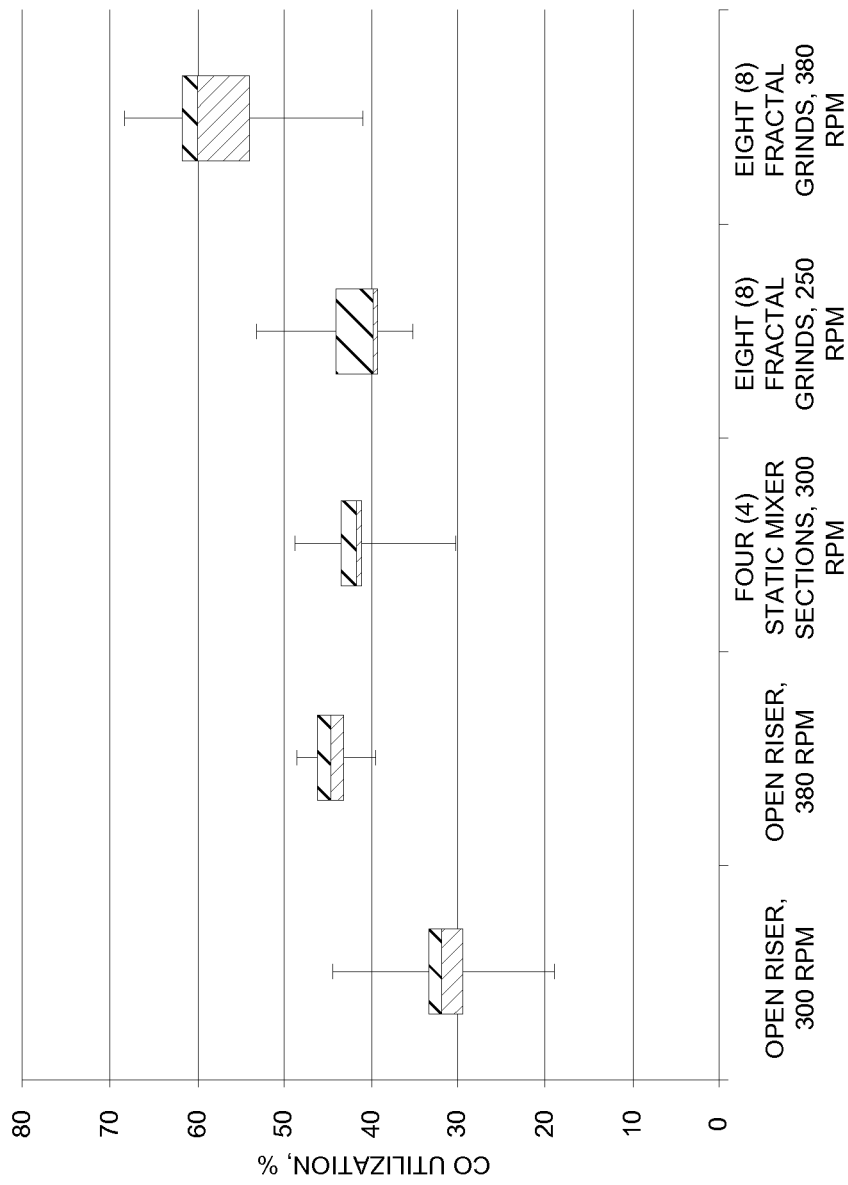
FIG. 6 compares CO utilization by bacteria in a circulated loop reactor at varying amounts of energy input (corresponding to varying loop pump speeds, or rpm), in the case of an open riser (i.e., no internal gas-liquid contacting devices), and in cases of a riser having static mixer sections and fractal grids.
Figure 7:
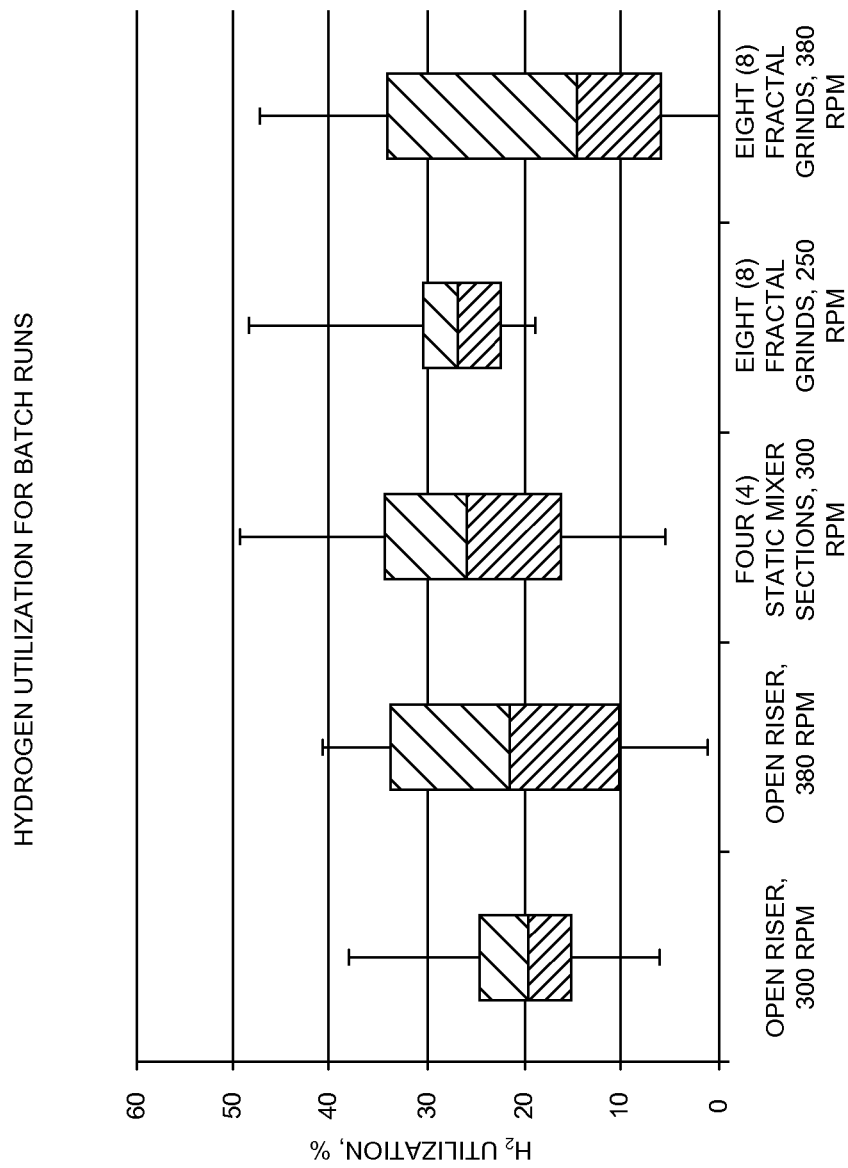
FIG. 7 compares $H_2$ utilization by bacteria in a circulated loop reactor at varying amounts of energy input (corresponding to varying loop pump speeds, or rpm), in the case of an open riser (i.e., no internal gas-liquid contacting devices), and in cases of a riser having internal static mixer sections or fractal grids.
Figure 8:
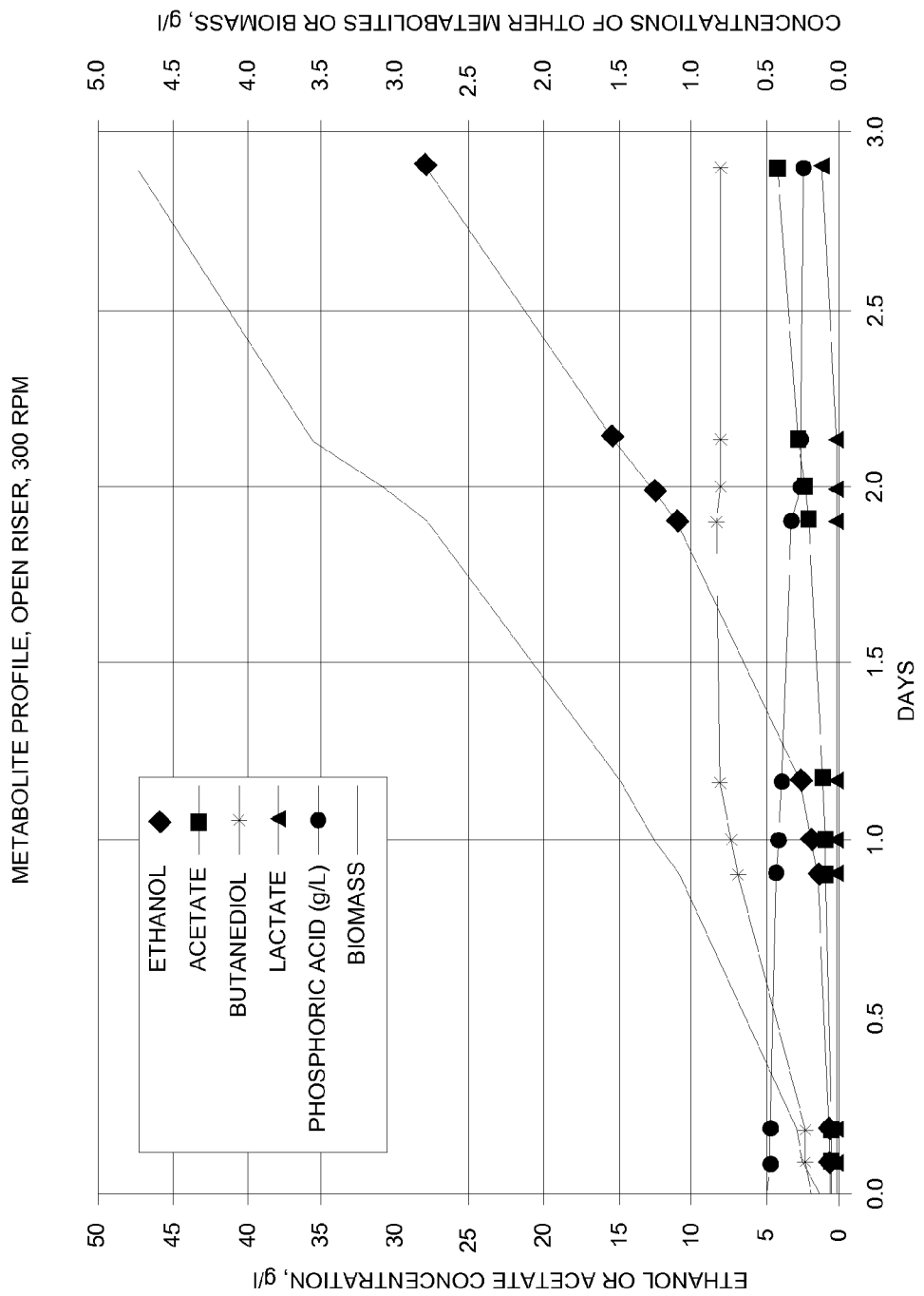
FIG. 8 provides a profile of metabolites over time in a culture medium, during the start-up of a biological CO conversion process in a circulated loop reactor, in the case of an open riser and 300 rpm loop pump speed.
Figure 9:
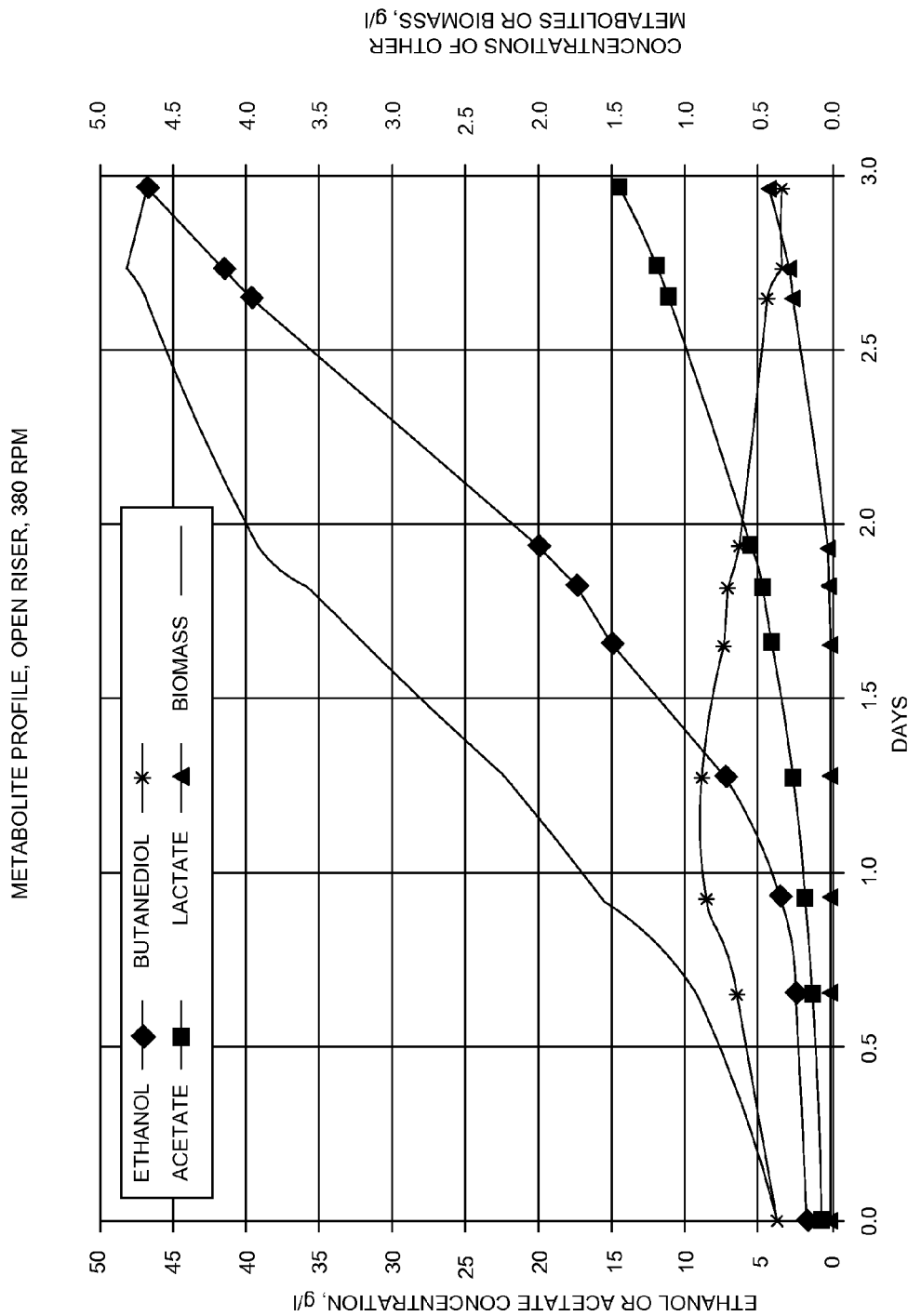
FIG. 9 provides a profile of metabolites over time in a culture medium, during the start-up of a biological CO conversion process in a circulated loop reactor, in the case of an open riser and 380 rpm loop pump speed.

FIGS. 6 and 7 show the CO utilization and $H_2$ utilization, respectively, obtained for the five experiments described above and summarized in the table. FIGS. 8 and 9 show the metabolite profiles obtained with an open riser at loop pump speeds of 300 rpm and 380 rpm (Runs 1 and 2), respectively. Although the same gas flows were used in these runs, the higher loop pump speed provided better CO utilization, as shown in FIG. 6. Due to this effect, an oversupplied state could be reached, giving a higher final ethanol concentration within the same time frame. Because of the lack of mixing in the riser with an open pipe, it is believed that the observed improvement in CO utilization at the higher loop pump speed was due to the higher level of entrainment of gas into the downcomer, thereby increasing the gas residence time within the loop.

Figure 10:
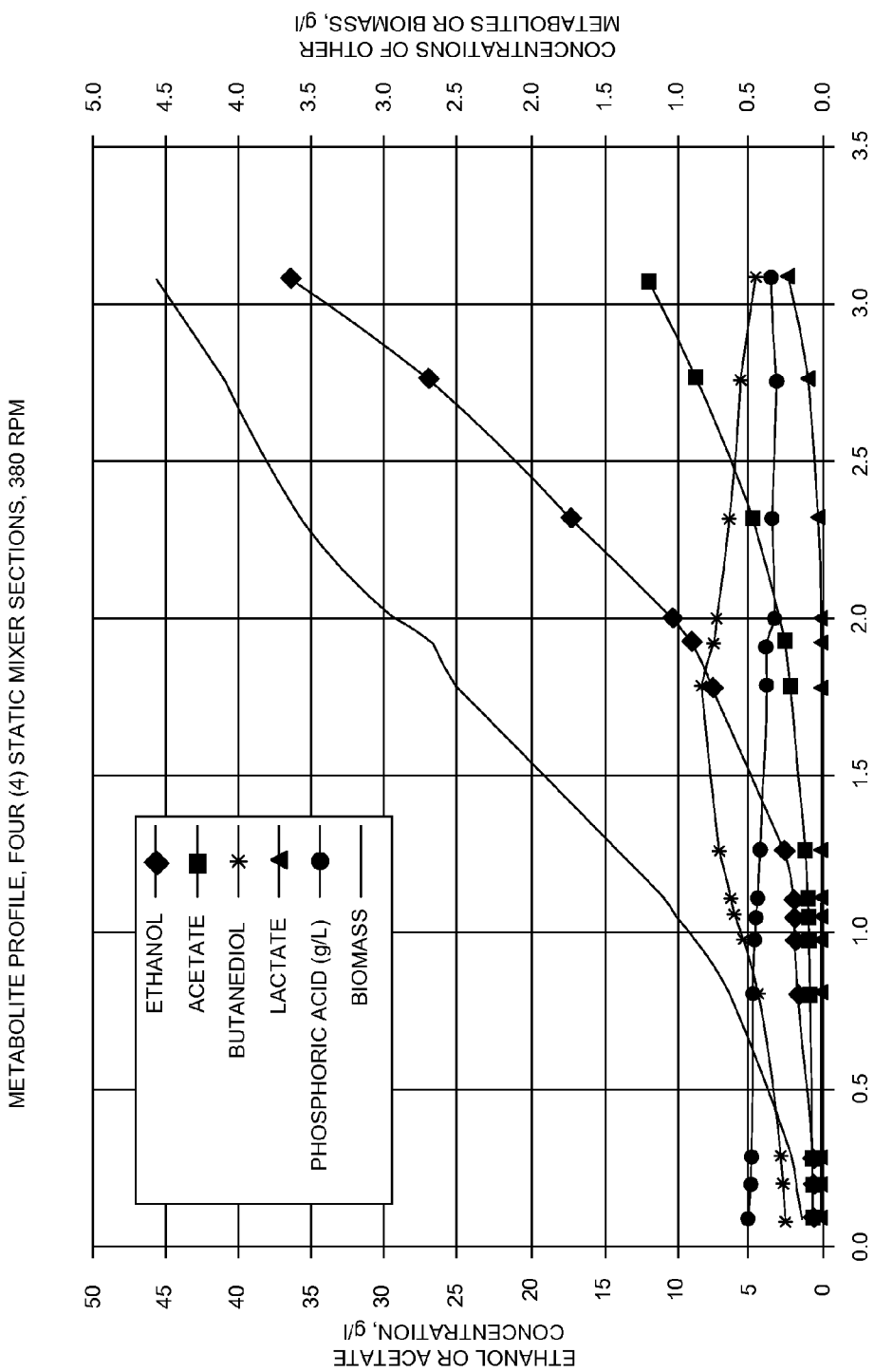
FIG. 10 provides a profile of metabolites over time in a culture medium, during the start-up of a biological CO conversion process in a circulated loop reactor, in the case of a riser having internal static mixer sections and using 380 rpm loop pump speed.

FIG. 10 shows the results obtained with four static mixer sections in the riser at a loop pump speed of 300 rpm (Run 3). The static mixers improved CO utilization, compared to the open riser configuration, when evaluated at the same loop pump speed and gas flow. This improvement is illustrated in FIG. 6. It was observed that the static mixers provided excellent bubble distribution within the riser and local mixing inside the sections.

Figure 11:
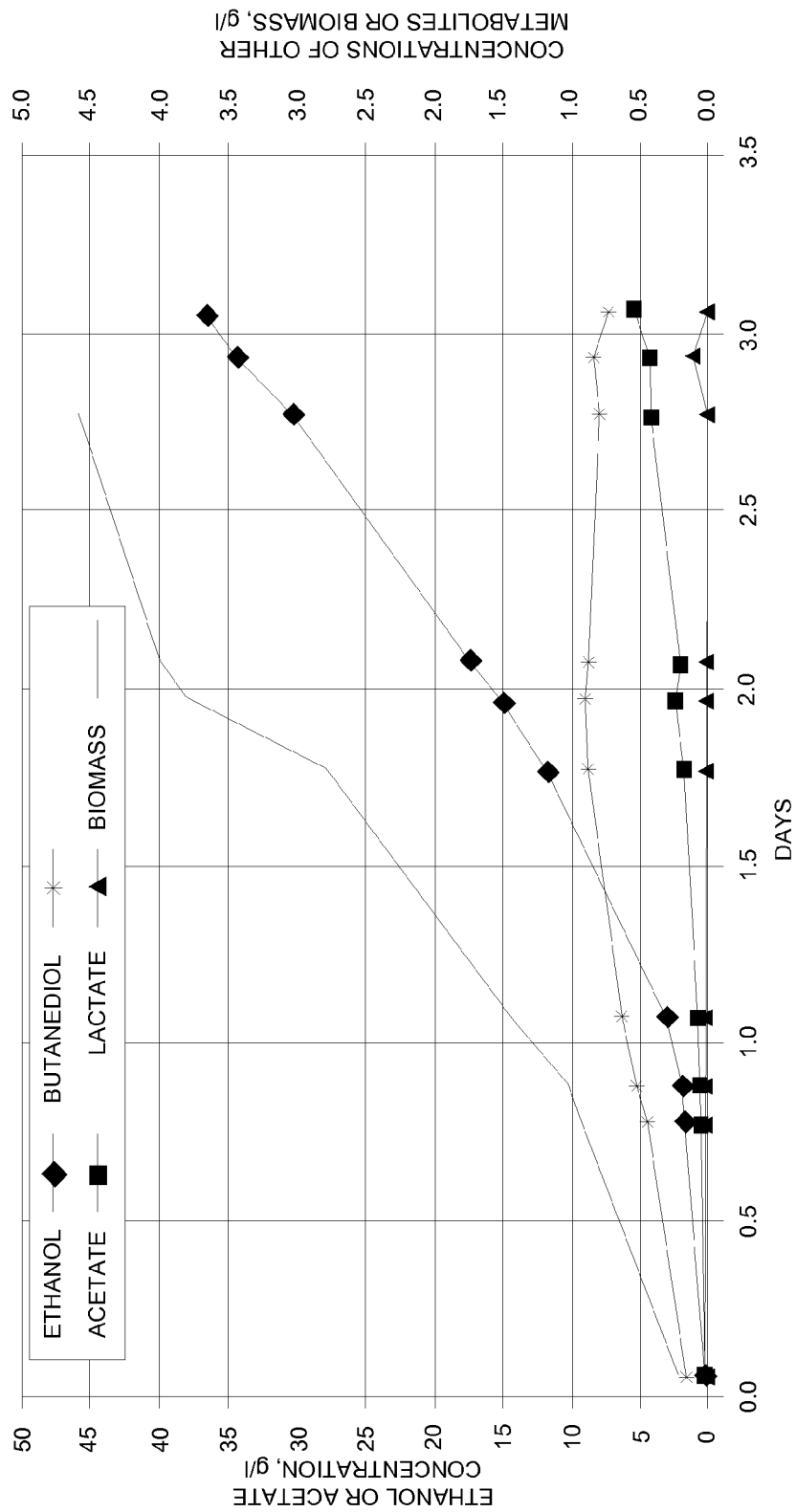
FIG. 11 provides a profile of metabolites over time in a culture medium, during the start-up of a biological CO conversion process in a circulated loop reactor, in the case of riser having internal fractal grids and 250 rpm loop pump speed.
Figure 12:
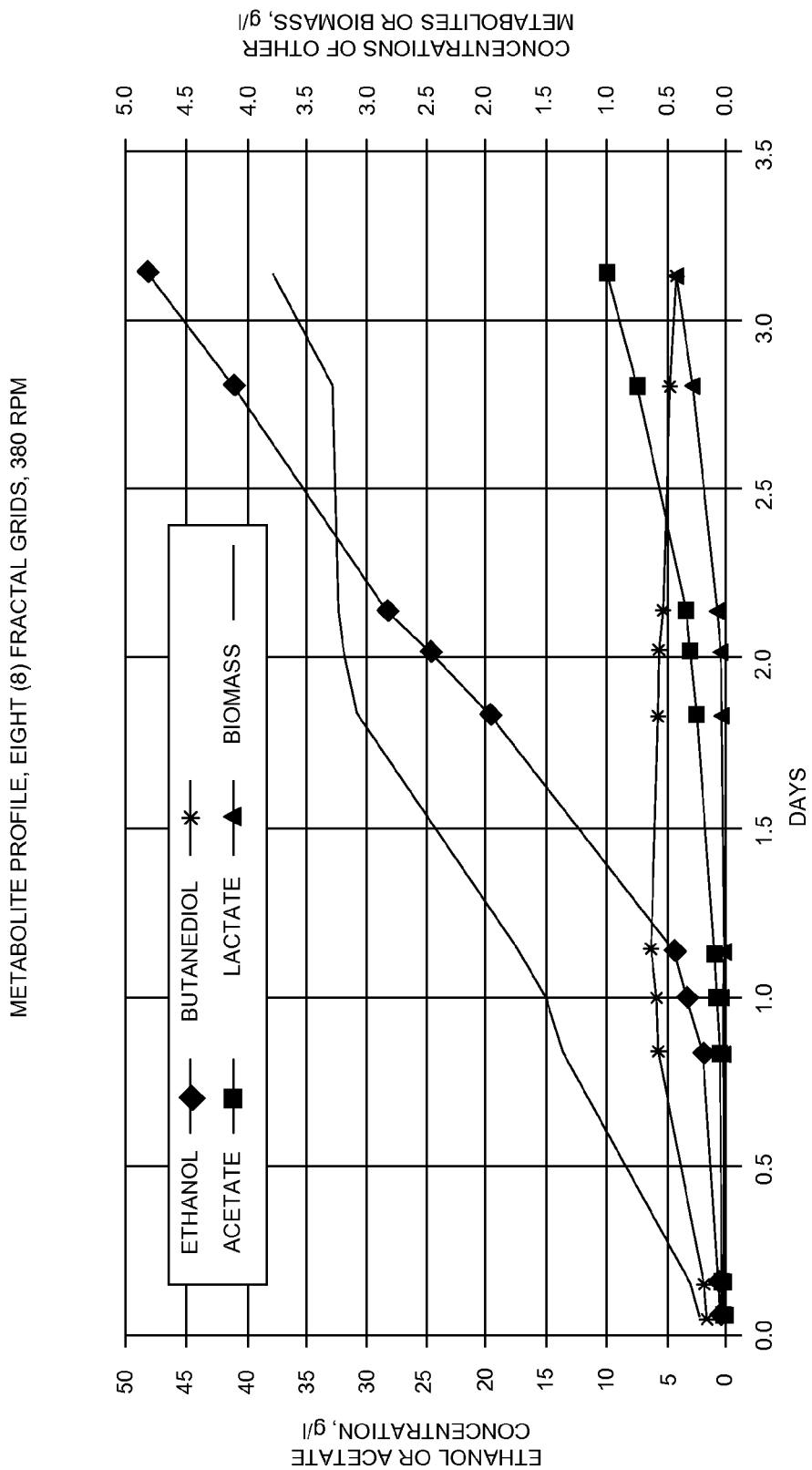
FIG. 12 provides a profile of metabolites over time in a culture medium, during the start-up of a biological CO conversion process in a circulated loop reactor, in the case of riser having internal fractal grids and 380 rpm loop pump speed.

FIGS. 11 and 12 show the metabolite profiles obtained with fractal grids in the riser at loop speeds of 250 rpm and 380 rpm, respectively (Runs 4 and 5). As shown in FIG. 11, a very similar metabolite profile was obtained using the fractal grids at a loop pump speed of 250 rpm, compared to that obtained using static mixers at 300 rpm (Run 4 vs. Run 3). In addition, a lower gas flow could be used to provide oversupply, in the case of using the fractal grids, at this lower pump speed. At the higher loop pump speed of 380 rpm (Run 5), much better results were obtained. As shown in FIG. 6, the gas utilization was greatly improved, and a much lower gas flow was sufficient to provide the desired oversupply. These results demonstrate that the use of the fractal grids as internals provided improved turbulence, resulting in improved mass transfer and, most importantly, significantly higher CO-utilization compared to the cases of using an open riser, or otherwise static mixers in the riser.

Using the fractal grids at a loop pump speed of 250 rpm (Run 4), small eddies were visible directly after the grids, but no larger eddies were visible further above the grids or in the headspace of the reactor. However, at the higher loop pump speed of 380 rpm (Run 5), larger eddies were seen, recirculating bubbles well above the top grid in the riser and also in the headspace.

Thus, three different mixing regimes were tested in a 15 liter forced loop bioreactor. From the two batch runs with an open riser, it was shown that higher loop pump speeds improved gas utilization, most likely due to a higher entrainment of gas through the downcomer, effectively increasing the gas residence time in the reactor. Fractal grids gave exceptional results, providing high turbulence in the riser to give oversupply of the bacterial culture at relatively lower gas flow rates. It is believed that one mechanism associated with this improvement is the formation of both large and small eddies, as a result of the fractal nature of the grids, thereby improving gas residence time in the loop and local mixing. From these results, it can be appreciated from comparing Runs 5 and 2 that CO utilization increased dramatically, by about 15%, i.e., 60% utilization vs. 45% utilization, relative to a base-case or reference process in which process conditions, including loop pump speed, were maintained the same, but without the use of the perforated plates or grids. While it is noted that the gas flow in Run 5 was lower (3.6 l/min, compared to 5.6 l/min in Run 2), the effect of performing both runs under the same reference conditions, including the use of the higher gas flow in Run 5, would only serve to further increase the CO utilization, i.e., beyond the 15% increase obtained in these results. This improvement in CO utilization has major implications for the process economics and overall competitiveness with existing routes for ethanol production.

Example 2

Extended Performance Testing, Fractal Grids Vs. Conventional Packing

Figure 13:
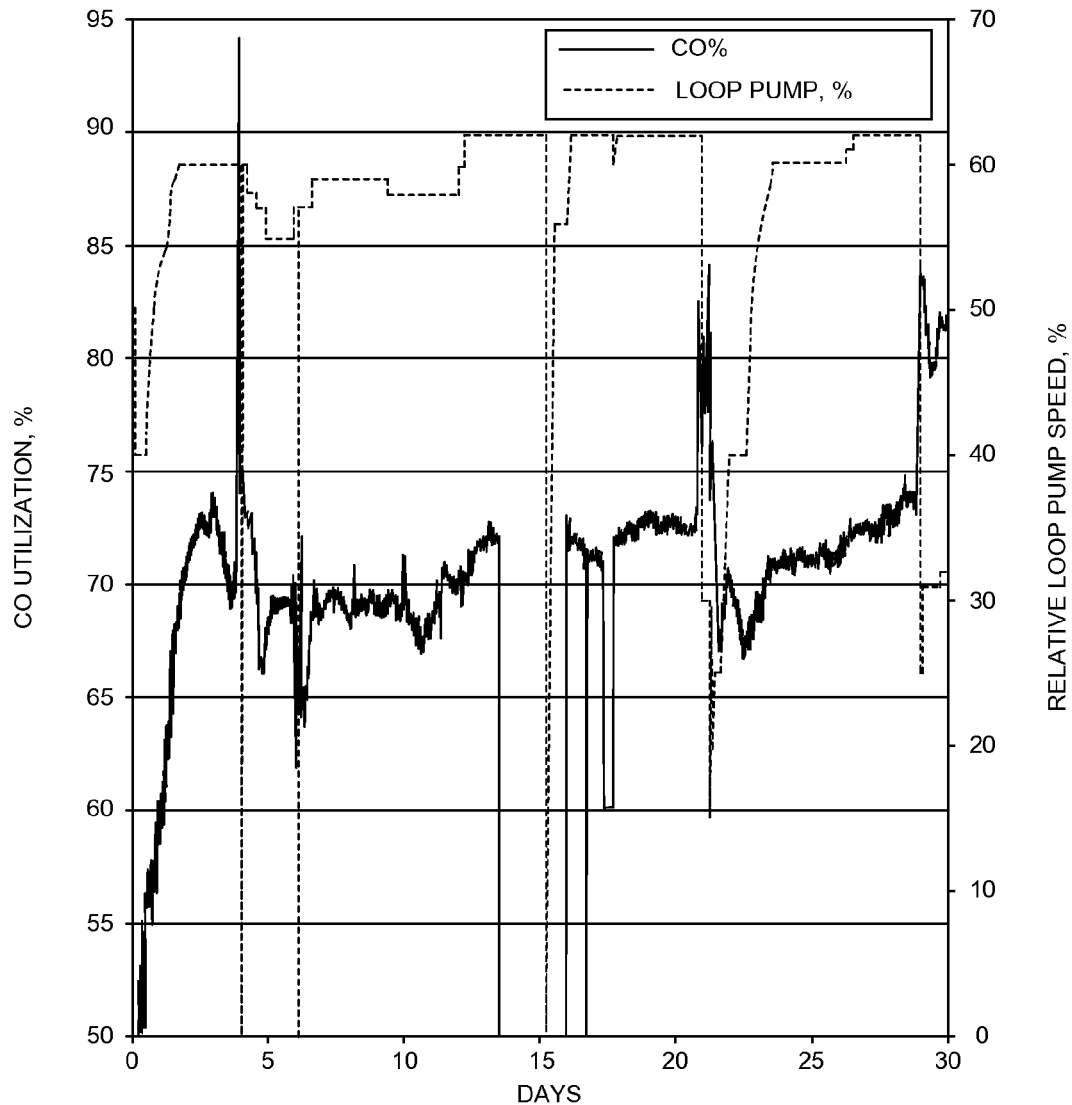
FIG. 13 illustrates the effect of changing loop pump speed on CO utilization by bacteria over 30 days of operation in a circulated loop reactor in the case of riser having internal static mixer sections.
Figure 14:
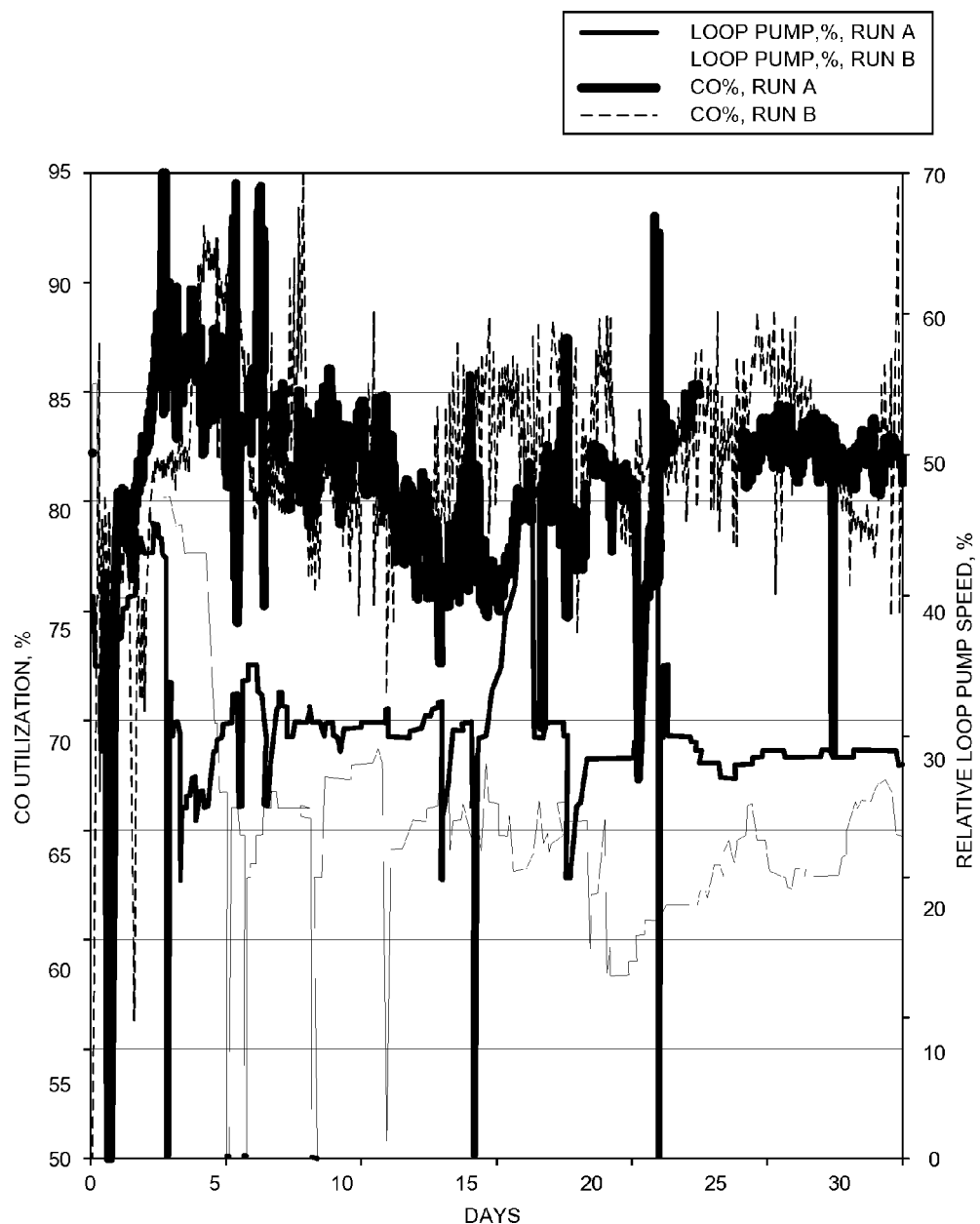
FIG. 14 illustrates the effect of changing loop pump speed on CO utilization by bacteria over 30 days of operation in a circulated loop reactor in the case of riser having internal fractal grids.

Further tests using a pilot plant scale, circulated loop reactor for the biological conversion of CO to ethanol were conducted to better evaluate the performance of the fractal grids, relative to conventional packing material used in gas-liquid contacting applications. The process features, including the bacterial culture, were as described with respect to Example 1 above, except for the use of a much larger circulated loop reactor of about 500 liters in volume. A key relationship for investigation was the effect of varying the loop pump speed on CO utilization. The loop pump speed is directly related to the amount of energy needed for circulation and represents a major operating cost of the biological conversion process. FIG. 13 shows this relationship over an extended, 30-day steady-state operating period in the case of using conventional structured packing material in the reactor riser. FIG. 14 shows the comparative, dramatic improvement in CO utilization, obtained in two additional 30-day steady-state operating periods conducted under the same operating conditions, but with fractal grids replacing the packing material.

As FIGS. 13 and 14 illustrate, during the extended operating periods, the fractal grids consistently achieved better CO utilization than the structured packing. For much of the operating period in which the performance of the fractal grids was evaluated (FIG. 14), CO utilization was in the range of 80-85%, despite the use of loop pump speeds in the range of only 20-30% of the pump capacity. Over a similar length of operation, evaluating the best-performing commercial structured packing for this biological conversion process, the CO utilization was only 70-75%, while running at loop pump speeds in the higher range of 55-60% of the pump capacity. Based on these results, the fractal grids provided significantly better gas utilization (an increase of 5-20%), even using only about half of the applied loop pump energy. Based on these results, it is expected that the energy requirements could be further reduced (e.g., reducing recirculation energy by even greater than 50%) to obtain a CO utilization comparable to that obtained in a reference process with no internals, i.e., an open riser.

What is claimed is:

1. A biological process for converting carbon monoxide (CO) into an end product, the process comprising:
   feeding a CO-containing substrate to a bioreactor containing carboxydotrophic bacteria in a liquid culture medium, to convert CO in the CO-containing substrate to the end product;
   wherein the bioreactor comprises a plurality of perforated plates arranged therein in substantially horizontal planes and each perforated plate comprising apertures through which the CO-containing substrate and liquid culture medium flow through the apertures providing a total open area of at least about 20% of the surface area of a plate, and at least some of the apertures providing at least three vertices for enhancing a CO utilization by the carboxydotrophic bacteria wherein the apertures of the respective plates are arranged in a fractal pattern having at least three scales of self-similarity, with the scales being separated by different distances said distances defined by the widths of solid surface portions defined by closed, elongated elements which separate the scales of apertures;
   wherein the CO utilization by the carboxydotrophic bacteria is increased by at least about 10%, relative to a reference biological process carried out in a bioreactor not containing the plurality of perforated plates.

2. The biological process of claim 1, wherein the apertures provide an open area from about 20% to about 50% of the surface area of the plate.

3. The biological process of claim 1, wherein the apertures of at least one perforated plate, include a large aperture having an open area of at least 3 times an open area of a small aperture of the at least one perforated plate.

4. The biological process of claim 3, wherein the apertures of the at least one perforated plate include at least three large apertures and at least three small apertures, each of the at least large apertures having an open area of at least 5 times an open area of each of the at least three small apertures.

5. The biological process of claim 1, wherein the apertures of at least one perforated plate, include an aperture providing at least 10 vertices.

6. The biological process of claim 5, wherein the apertures of the at least one perforated plate comprise at least three apertures, each aperture providing at least 50 vertices.

7. The biological process of claim 1, wherein the apertures of at least one perforated plate, include an aperture formed predominantly by line segments having a length of less than about 20% of the perimeter of the aperture.

8. The biological process of claim 7, wherein the at least one perforated plate comprises at least 3 apertures, the apertures characterized in that at least about 80% of the perimeters of the apertures are formed by line segments having a length of less than about 10% of the respective perimeters of the apertures.

9. The biological process of claim 1, wherein the plurality of perforated plates includes comprise at least three perforated plates spaced apart axially at distances ranging from about 0.01 meters to about 1 meter.

10. The biological process of claim 9, wherein the at least three perforated plates are spaced apart axially at distances ranging from about 0.05 meters to about 0.5 meters.

11. The biological process of claim 1, wherein the plurality of perforated plates are arranged in a riser section of the bioreactor and wherein the bioreactor comprises an outlet port above a top plate, through which gases exit the bioreactor, and a recirculation loop that returns liquid culture medium from above the top plate to a lower section of the bioreactor.

12. The biological process of claim 11, wherein the recirculation loop returns liquid culture medium from above the top plate, through a downcomer, and to a lower section of the bioreactor below a bottom plate.

13. The biological process of claim 1, wherein the CO utilization by the carboxydotrophic bacteria is at least about 70%.

14. The biological process of claim 1, wherein CO utilization by the carboxydotrophic bacteria is increased by at least about 15%, relative to a reference biological process carried out in a bioreactor not containing the plurality of perforated plates.

15. The biological process of claim 1, which is carried out at a pressure of less than 100 psig.

16. A biological process for converting carbon monoxide (CO) to ethanol, the process comprising:
   feeding a CO-containing substrate to a bioreactor containing carboxydotrophic bacteria in a liquid culture medium, to convert CO in the CO-containing substrate to ethanol and other metabolites, wherein the bioreactor includes a riser section having a plurality of perforated plates arranged therein in substantially horizontal planes, an outlet port through which gases exit the bioreactor, the outlet port disposed above a top plate of the plurality of perforated plates, and a recirculation loop that returns liquid culture medium from above the top plate to a lower section of the bioreactor,
   wherein the CO-containing substrate and liquid culture medium flow upward through apertures in the plurality of perforated plates, wherein the apertures of the respective plates are arranged in a fractal pattern having at least three scales of self-similarity, with the scales being separated at different distances, said distances defined by the widths of solid surface portions defined by closed, elongated elements which separate the scales of apertures, and wherein the apertures provide at least three vertices for enhancing CO utilization by the carboxydotrophic bacteria;
   wherein the CO utilization by the carboxydotrophic bacteria is at least about 70% and is increased by at least about 15%, relative to a reference biological process carried out in a bioreactor not containing the plurality of perforated plates, and
   wherein the biological process is carried out at a pressure from about 0 psig to about 100 psig.

* * * * *